(12) United States Patent
Scott et al.

(10) Patent No.: US 7,939,642 B2
(45) Date of Patent: May 10, 2011

(54) ANTIBODY AND USES THEREOF

(75) Inventors: Christopher Scott, Belfast (IE); Roberta Burden, Belfast (IE); Shane Olwill, Belfast (IE); Brian Walker, Belfast (IE); Jim Johnston, Belfast (IE)

(73) Assignee: Fusion Antibodies Limited (GB)

( * ) Notice: Subject to any disclaimer, the term of this patent is extended or adjusted under 35 U.S.C. 154(b) by 302 days.

(21) Appl. No.: 11/918,102

(22) PCT Filed: Apr. 10, 2006

(86) PCT No.: PCT/GB2006/001314
§ 371 (c)(1),
(2), (4) Date: Jan. 9, 2008

(87) PCT Pub. No.: WO2006/109045
PCT Pub. Date: Oct. 19, 2006

(65) Prior Publication Data
US 2009/0068198 A1 Mar. 12, 2009
US 2009/0317405 A2 Dec. 24, 2009

(30) Foreign Application Priority Data

Apr. 9, 2005 (GB) .................................. 0507219.4
Apr. 11, 2005 (GB) .................................. 0507272.3

(51) Int. Cl.
*C12P 21/08* (2006.01)
(52) U.S. Cl. .................................. 530/387.3; 530/387.1
(58) Field of Classification Search .......................... None
See application file for complete search history.

(56) References Cited

U.S. PATENT DOCUMENTS
2001/0044414 A1* 11/2001 Clark et al. ..................... 514/44

FOREIGN PATENT DOCUMENTS
| WO | 93/08300 | 4/1993 |
| WO | 99/58153 | 11/1999 |
| WO | 0228904 | 4/2002 |
| WO | 2005/026211 | 3/2005 |

OTHER PUBLICATIONS (Paul, Fundamental Immunology, 3rd Edition, 1993, pp. 292-295, under the heading "Fv Structure and Diversity in Three Dimensions").*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
XP-002396489, Masao et al., "Immunoglobulin VL Region of anti-human fas mouse monoclonal antibody CHII,", Abstract only, Jul. 27, 1999.
XP-002328829, Thurmond et al., "Identification of a Potent and Selective Noncovalent Cathepsin S Inhibitor", The Journal of Pharmacology and Experimental Therapeutics, The American Society for Pharmacology and Experimental Therapeutics, JPET 308:268-276, 2000.
Thurmond et al. "Cathepsin S. Inhibitors as novel immunomodulators" Current Opinion In Investigation Drugs (London, England, 2002) vol. 6 No. 5, May 2005 pp. 473-482.
XP-001247292, Liu Weimin et al., "Cysteine protease cathepsin S as a key step in antigen presentation", Drug News & Perspectives, Jul.-Aug. 2004, vol. 17, No. 6, Jul. 2004, pp. 357-363.
Shi, G,-P. et al., "Deficiency of the Crysteine Protease Cathepsin S Impairs Microvessel Growth," *Circulation Research*, Mar. 21, 2003, downloaded from circes.ahajournals.org at European Patent Office, 8 pages.
Thurmond, R.L. et al., "Cathepsin S Inhibitors as Novel Immunomodulators," *Current Opinion in Investigational Drugs*, 2005, vol. 6, No. 5, pp. 473-482.

* cited by examiner

*Primary Examiner* — Sheela J Huff
(74) *Attorney, Agent, or Firm* — DLA Piper LLP (US)

(57) ABSTRACT

Described are specific binding members e.g. antibodies which may be used in the treatment of diseases associated with cathepsin S activity. The specific binding members binds cathepsin S and inhibits its proteolytic activity. The binding members may be used in the treatment of diseases such as cancer, inflammatory diseases, neurodegenerative disorders, autoimmune disorders, and other diseases associated with excessive, deregulated or inappropriate angiogenesis.

9 Claims, 27 Drawing Sheets

| | Ag | 1 | 2 | 3 | 4 | 5 | 6 | 7 | 8 | 9 | 10 | 11 | 12 |
|---|---|---|---|---|---|---|---|---|---|---|---|---|---|
| A | + | 3.784 | 3.546 | 3.267 | 3.731 | 3.258 | 3.627 | 3.354 | 3.852 | 3.703 | 3.698 | 3.512 | 0.032 |
| B | - | 0.231 | 0.311 | 0.268 | 0.316 | 0.275 | 0.233 | 0.231 | 0.298 | 0.271 | 0.261 | 0.253 | 0.031 |
| C | + | 3.246 | 3.533 | 3.644 | 3.650 | 3.632 | 3.112 | 3.632 | 2.932 | 3.356 | 3.773 | 3.632 | 0.035 |
| D | - | 0.411 | 0.363 | 0.311 | 0.389 | 0.284 | 0.275 | 0.387 | 0.314 | 0.253 | 0.234 | 0.365 | 0.029 |
| E | + | 3.631 | 3.457 | 3.751 | 3.734 | 3.965 | 3.111 | 2.934 | 2.885 | 3.124 | 3.742 | 3.749 | 0.025 |
| F | - | 0.247 | 0.311 | 0.385 | 0.487 | 0.311 | 0.410 | 0.296 | 0.257 | 0.396 | 0.373 | 0.263 | 0.033 |
| G | + | 3.441 | 3.864 | 3.862 | 3.258 | 2.963 | 2.814 | 3.567 | 3.853 | 3.843 | 3.546 | 3.743 | 0.027 |
| H | - | 0.280 | 0.342 | 0.234 | 0.296 | 0.203 | 0.301 | 0.245 | 0.321 | 0.250 | 0.276 | 0.268 | 0.026 |

Figure 6

| Ab. | A<br>IgG1 | B<br>IgG2a | C<br>IgG2b | D<br>Ig | E<br>Ig | F<br>IgM | G<br>Kappa | H<br>Lambda |
|---|---|---|---|---|---|---|---|---|
| 1* | 1.394 | 0.134 | 0.115 | 0.248 | 0.116 | 0.09 | 1.361 | 0.057 |
| 2 | 1.44 | 0.113 | 0.125 | 0.253 | 0.125 | 0.074 | 1.49 | 0.057 |
| 3 | 1.469 | 0.121 | 0.13 | 0.254 | 0.117 | 0.082 | 1.218 | 0.057 |
| 4 | 0.147 | 0.11 | 0.092 | 0.23 | 0.119 | 1.639 | 1.731 | 0.057 |
| 5 | 1.556 | 0.134 | 0.128 | 0.25 | 0.122 | 0.081 | 1.311 | 0.057 |
| 6 | 0.114 | 0.65 | 0.084 | 0.216 | 0.101 | 1.534 | 1.395 | 0.057 |

Figure 10.

Consensus Protein Sequence for VH

VQLQESGGGVLVKPGGSLKLSCAASGFAFSSYDMSWVRQTPEKRLEWVA
YITTGGVNTYYPDTVKGRFTISRDNAKNTLYLQMSSLKSEDTAMYYCARHSYFDYW
GQGTTVTVSS  (SEQ ID NO: 7)

Consensus Protein Sequence for VL

DVLMTQTPLSLPVSLGDQASISCRSSQSLVHSNGNTYLHWYLQKPGQSPKLLI
YKVSNRFSGVPDRFSGSGSGTDFTLKISRVEAEDLGVYFCSQTTHVPPTFGSG
TKLEIKR  (SEQ ID NO: 8)

Figure 20

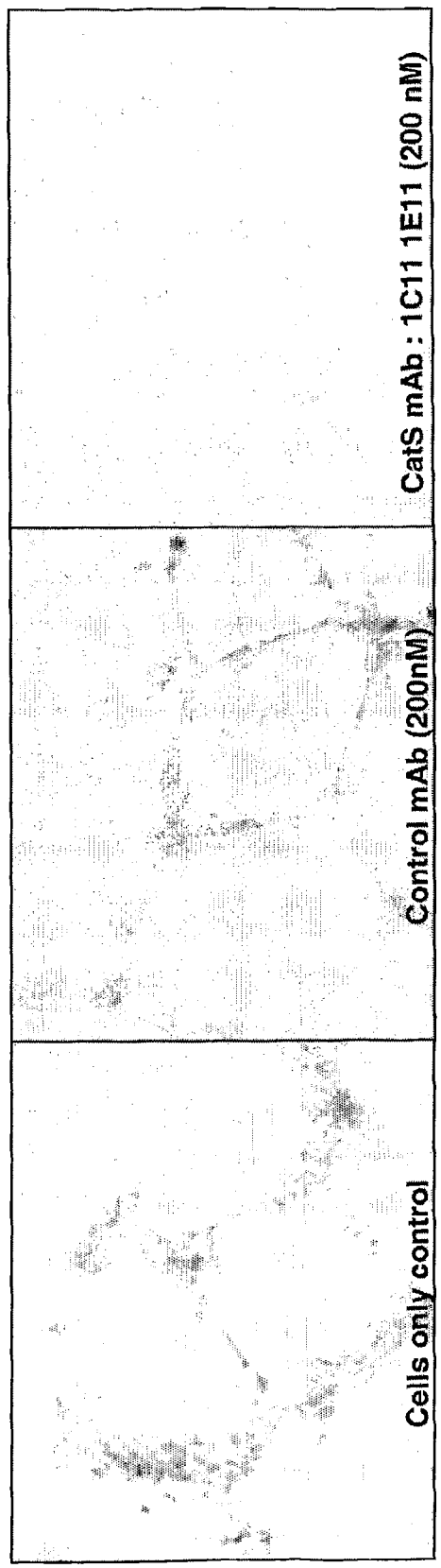
Figure 27   *In vitro* angiogenesis assay using primary HUVEC cells

ANTIBODY AND USES THEREOF

TECHNICAL FIELD

This application relates to a specific binding member and its use in methods of treatment. In particular, it relates to specific binding members to cathepsin S, preferably specific binding members which inhibit the proteolytic activity of cathepsin S.

BACKGROUND

Proteases are a large group of proteins that comprise approximately 2% of all gene products (Rawlings and Barrett, 1999). Proteases catalyse the hydrolysis of peptide bonds and are vital for the proper functioning of all cells and organisms. Proteolytic processing events are important in a wide range of cellular processes including bone formation, wound healing, angiogenesis and apoptosis.

The lysosomal cysteine proteases were initially thought to be enzymes that were responsible for non-selective degradation of proteins in the lysosomes. They are now known to be accountable for a number of important cellular processes, having roles in apoptosis, antigen presentation, coagulation, digestion, pro-hormone processing and extracellular matrix remodelling (Chapman et al, 1997).

Cathepsin S (Cat S) is a member of the papain superfamily of lysosomal cysteine proteases. To date, eleven human cathepsins have been identified, but the specific in vivo roles of each are still to be determined (Katunuma et al, 2003). Cathepsins B, L, H, F, O, X and C are expressed in most cells, suggesting a possible role in regulating protein turnover, whereas Cathepsins S, K, W and V are restricted to particular cells and tissues, indicating that they may have more specific roles (Kos et al, 2001; Berdowska, 2004).

Cat S was originally identified from bovine lymph nodes and spleen and the human form cloned from a human macrophage cDNA library (Shi et al, 1992). The gene encoding Cat S is located on human chromosome 1q21. The 996 base pair transcript encoded by the Cat S gene, is initially translated into an unprocessed precursor protein with a molecular weight of 37.5 kDa. The unprocessed protein is composed of 331 amino acids; a 15 amino acid signal peptide, a 99 amino acid pro-peptide sequence and a 217 amino acid peptide. Cat S is initially expressed with a signal peptide that is removed after it enters the lumen of the endoplasmic reticulum. The propeptide sequence binds to the active site of the protease, rendering it inactive until it has been transported to the acidic endosomal compartments, after which the propeptide sequence is removed and the protease is activated (Baker et al, 2003).

Cat S has been identified as a key enzyme in major histocompatibility complex class II (MHC-II) mediated antigen presentation, by cleavage of the invariant chain, prior to antigen loading. Studies have shown that mice deficient in Cat S have an impaired ability to present exogenous proteins by APC's (Nakagawa et al, 1999). The specificity of Cat S in the processing of the invariant chain Ii, allows for Cat S specific therapeutic targets in the treatment of conditions such as asthma and autoimmune disorders (Chapman et al, 1997).

Pathological Association of Cat S

Alterations in protease control frequently underlie many human pathological processes. The deregulated expression and activity of the lysosomal cysteine protease Cathepsin S has been linked to a range of conditions including neurodegenerative disorders, autoimmune diseases and certain malignancies.

Cat S upregulation has been linked to several neurodegenerative disorders. It is believed to have a role in the production of the β peptide (Aβ) from the amyloid precursor protein (APP) (Munger et al, 1995) and its expression has been shown to be upregulated in both Alzheimer's Disease and Down's Syndrome (Lemere et al, 1995). Cat S may also have a role in Multiple Sclerosis through the ability of Cat S to degrade myelin basic protein, a potential autoantigen implicated in the pathogenesis of MS (Beck et al, 2001) and in Creutzfeldt-Jakob disease (CJD) patients, Cat S expression has been shown to increase more than four fold (Baker et al, 2002).

Aberrant Cat S expression has also been associated with atherosclerosis. Cat S expression is negligible in normal arteries, yet human atheroma display strong immunoreactivity (Sukhova et al, 1998). Further studies using knockout mice, deficient in both Cat S and the LDL-receptor, were shown to develop significantly less atherosclerosis (Sukhova et al, 2003). Further research has linked Cat S expression with inflammatory muscle disease and rheumatoid arthritis. Muscle biopsy specimens from patients with inflammatory myopathy had a 10 fold increase in Cat S expression compared to control muscle sections (Wiendl et al, 2003), and levels of Cat S expression were significantly higher in synovial fluid from patients with rheumatoid arthritis compared to those with osteoarthritis (Hashimoto et al, 2001).

The role of Cat S has also been investigated in specific malignancies. The expression of Cat S was shown to be significantly greater in lung tumour and prostate carcinomas sections in comparison to normal tissue (Kos et al, 2001, Fernandez et al, 2001) and suggested that Cat S may have a role in tumour invasion and disease progression.

Recent work in this laboratory on Cat S demonstrated the significance of its expression in human astrocytomas (Flannery et al, 2003). Immunohistochemical analysis showed the expression of Cat S in a panel of astrocytoma biopsy specimens from WHO grades I to IV, but appeared absent from normal astrocytes, neurones, oligodendrocytes and endothelial cells. Cat S expression appeared highest in grade IV tumours and levels of extracellular activity were greatest in cultures derived from grade IV tumours.

Cat S has been shown to be active in the degradation of ECM macromolecules such as laminin, collagens, elastin and chondroitin sulphate proteoglycans (Liuzzo et al, 1999).

The generation of inhibitors specifically targeting Cat S have potential as therapeutic agents for alleviations of the symptoms associated with the activity of this protease.

Inhibition of Cat S

When proteases are over-expressed, therapeutic strategies have focused on the development of inhibitors to block the activity of these enzymes. The generation of specific small molecule inhibitors to the cathepsins have proved difficult in the past, due to problems with selectivity and specificity. The dipeptide α-keto-β-aldehydes developed as potent reversible inhibitors to Cat S by Walker et al, had the ability to inhibit Cat B and L, albeit with less efficiency (Walker et al, 2000), and the Cat S inhibitor 4-Morpholineurea-Leu-HomoPhe-vinylsulphone (LHVS) has also been shown to inhibit other cathepsins when used at higher concentrations (Palmer et al, 1995).

SUMMARY

As described herein, we have developed a monoclonal antibody with specificity for cathepsin S which potently inhibits the proteolytic activity of cathepsin S, and moreover, inhibits tumour cell invasion and angiogenesis. We have identified the VH and VL domains and CDRs of the antibody. This is the first demonstration of a cathepsin S specific antibody directly inhibiting the protease activity of cathepsin S and thus uniquely enables the use of such antibodies as active therapeutic agents with a wide range of applications from cancer therapeutics to anti-inflammatory agents with high specificity and low toxicity.

Accordingly, in a first aspect, we provide a specific binding member which binds cathepsin S and inhibits its proteolytic activity.

In one embodiment, the specific binding member comprises an antigen binding domain comprising at least one of the CDRs with an amino acid sequence selected from the group consisting of Seq ID No: 1, Seq ID No: 2, Seq ID No: 3, or a variant thereof and/or at least one of the CDRs with an amino acid sequence consisting of Seq ID No: 4, Seq ID No: 5 and Seq ID No: 6, or a variant thereof.

The amino acid sequences corresponding to SEQ ID NOS: 1-6 are as follows:

```
Seq ID No: 1:
SYDMS

Seq ID No: 2:
YITTGGVNTYYPDTVKG

Seq ID No: 3
HSYFDY

Seq ID No: 4:
RSSQSLVHSNGNTYLH

Seq ID No: 5:
KVSNRFS

Seq ID No: 6:
SQTTHVPPT
```

In one embodiment of the first aspect of the disclosure, the specific binding member comprises an antigen binding domain comprising at least one of the CDRs with an amino acid sequence selected from the group consisting of Seq ID No: 1, Seq ID No: 2, Seq ID No: 3, and/or at least one of the CDRs with an amino acid sequence consisting of Seq ID No: 4, Seq ID No: 5 and Seq ID No: 6.

In an embodiment, the specific binding member comprises an antigen binding domain comprising at least one, for example at least two or all three of the CDRs with an amino acid sequence selected from the group consisting of Seq ID No: 1, Seq ID No: 2, Seq ID No: 3, or variants thereof and at least one, for example at least two, for example all three of the CDRs with an amino acid sequence consisting of Seq ID No: 4, Seq ID No: 5 and Seq ID No: 6, or variants thereof.

In a particular embodiment, the specific binding member comprises a CDR having the amino acid sequence SEQ ID NO: 5, or a variant thereof and/or the CDR having the amino acid sequence SEQ ID NO: 6, or a variant thereof.

In one embodiment, the specific binding member comprises an antibody $V_H$ domain or an antibody $V_L$ domain, or both.

In one embodiment, the specific binding the antibody $V_H$ domain comprises at least one of the CDRs, for example two or three CDRs, with an amino acid sequence selected from the group consisting of Seq ID No: 1, Seq ID No: 2, Seq ID No: 3, and/or the antibody $V_L$ domain comprises at least one of the CDRs, for example two or three CDRs, with an amino acid sequence consisting of Seq ID No: 4, Seq ID No: 5 and Seq ID No: 6.

In a preferred embodiment, the antibody $V_L$ domain comprises the amino acid sequence Seq ID No: 8 and/or the antibody $V_H$ domain comprises the amino acid sequence Seq ID No: 7.

```
Seq ID No: 7:
VQLQESGGVLVKPGGSLKLSCAASGFAFSSYDMSWVRQTPEKRLEWVAYI

TTGGVNTYYPDTVKGRFTISRDNAKNTLYLQMSSLKSEDTAMYYCARHSY

FDYWGQGTTVTVSS

Seq ID No: 8:
DVLMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQTTHVP

PTFGSGTKLEIKR
```

The specific binding member may be an antibody, for example a whole antibody.

In one alternative embodiment, the specific binding member may be an antibody fragment such as an scFv.

The provision of the specific binding members of our disclosure enables the development of related antibodies which also inhibit the proteolytic activity of cathepsin S and which optionally have similar or greater binding specificity.

Accordingly, further encompassed within the scope of the first aspect of our disclosure are specific binding members comprising at least one of the CDRs with an amino acid sequence selected from the group consisting of Seq ID No: 1, Seq ID No: 2, Seq ID No: 3, and/or at least one of the CDRs with an amino acid sequence consisting of Seq ID No: 4, Seq ID No: 5 and Seq ID No: 6, in which 5 or less, for example 4, 3, 2, or 1 amino acid substitutions have been made in at least one CDR and wherein the specific binding member retains the ability to inhibit the proteolytic activity of cathepsin S.

The specific binding member of the first aspect of our disclosure has the ability to inhibit tumour cell invasion.

In another embodiment, the specific binding member of the first aspect of our disclosure has the ability to inhibit angiogenesis.

In a second aspect of our disclosure, there is provided a nucleic acid encoding a specific binding member according to the first aspect of our disclosure.

The nucleic acid may be used to provide specific binding members according to the first aspect of our disclosure. Accordingly, there is provided a method of producing a specific binding member capable of inhibiting the proteolytic activity of cathepsin S, said method comprising expressing the nucleic acid according to the second aspect of our disclosure in a host cell and isolating said specific binding member from said cell.

We further provide a pharmaceutical composition comprising a specific binding member of the first aspect of our disclosure or a nucleic acid of the second aspect of our disclosure.

The specific binding members, nucleic acids or compositions may be used for the inhibition of cathepsin S activity, in particular where the cathepsin S is aberrantly active. Typically, in non-disease states, cathepsin S is localised intracellularly, within lysosomes. However, in certain disease states, cathepsin S is secreted from cells.

Accordingly, in a further aspect, we provide a method of inhibiting cathepsin S in a biological sample, said method comprising administration of a specific binding member according to the first aspect of our disclosure or a nucleic acid according to the second aspect of our disclosure.

In a further aspect, there is provided a method of treating a condition associated with activity of cathepsin S in a patient in need of treatment thereof, said method comprising administration of a specific binding member according to the first aspect of our disclosure or a nucleic acid according to the second aspect of our disclosure.

In one embodiment, condition is a condition associated with aberrant activity of cathepsin S.

In the context of the present application, cathepsin S is considered to be aberrantly active where its expression or localisation differs from that of normal healthy cells, for example overexpression and/or secretion from a cell which, typically, does not secrete cathepsin S, extracellular localisation, cell surface localisation, in which cathepsin S is not normally expressed at the cell surface, or secretion or expression which is greater than normal at or from a cell or tissue and where its activity contributes to a disease state.

Further provided is a specific binding member according to the first aspect of our disclosure or a nucleic acid according to the second aspect of our disclosure for use in medicine.

We further provide a specific binding member according to the first aspect of our disclosure or a nucleic acid according to the second aspect of our disclosure for use in treatment of a condition associated with aberrant cathepsin S activity.

Also provided is the use of a specific binding member according to the first aspect of our disclosure or a nucleic acid according to the second aspect of our disclosure in the preparation of a medicament for the treatment of a condition associated with aberrant activity expression of cathepsin S.

Our disclosure may be used in the treatment of any condition with which aberrant activity of cathepsin S is associated, in particular conditions associated with expression of cathepsin S. For example, conditions in which our disclosure may be used include, but are not limited to neurodegenerative disorders, for example Alzheimer's disease and multiple sclerosis, autoimmune disorders, inflammatory disorders, for example inflammatory muscle disease, rheumatoid arthritis and asthma, atherosclerosis, neoplastic disease, and other diseases associated with excessive, deregulated or inappropriate angiogenesis.s.

DETAILED DESCRIPTION

Binding Members

In the context of our disclosure, a "binding member" is a molecule which has binding specificity for another molecule, the molecules constituting a pair of specific binding members. One member of the pair of molecules may have an area which specifically binds to or is complementary to a part or all of the other member of the pair of molecules. We are particularly concerned with antigen-antibody type reactions.

In the context of our disclosure, an "antibody" should be understood to refer to an immunoglobulin or part thereof or any polypeptide comprising a binding domain which is, or is homologous to, an antibody binding domain. Antibodies include but are not limited to polyclonal, monoclonal, monospecific, polyspecific antibodies and fragments thereof and chimeric antibodies comprising an immunoglobulin binding domain fused to another polypeptide.

Intact (whole) antibodies comprise an immunoglobulin molecule consisting of heavy chains and light chains, each of which carries a variable region designated VH and VL, respectively. The variable region consists of three complementarity determining regions (CDRs, also known as hypervariable regions) and four framework regions (FR) or scaffolds. The CDR forms a complementary steric structure with the antigen molecule and determines the specificity of the antibody.

Fragments of antibodies may retain the binding ability of the intact antibody and may be used in place of the intact antibody. Accordingly, for the purposes of our disclosure, unless the context demands otherwise, the term "antibodies" should be understood to encompass antibody fragments. Examples of antibody fragments include Fab, Fab', F (ab')$_2$, Fd, dAb, and Fv fragments, scFvs, bispecific scFvs, diabodies, linear antibodies (see U.S. Pat. No. 5,641,870, Example 2; Zapata et al., Protein Eng 8 (10): 1057-1062 [1995]); single-chain antibody molecules; and multispecific antibodies formed from antibody fragments.

The Fab fragment consists of an entire L chain (VL and CL), together with VH and CH1. Fab' fragments differ from Fab fragments by having additional few residues at the carboxy terminus of the CH1 domain including one or more cysteines from the antibody hinge region. The F (ab') 2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993)).

Further encompassed by fragments are individual CDRS.

The amino acid sequences of the VH and VL regions of the intact antibody 1E11 with specificity for Cat S has been identified. Furthermore, we have identified the six CDRs of this antibody (Seq ID Nos: 1, 2, 3, 4, 5 and 6).

As described above, the specific binding members of our disclosure is not limited to the specific sequences of the 1E11 antibody, the VH, VL and the CDRs having the sequences disclosed herein but also extends to variants thereof which maintain the ability to inhibit the proteolytic activity of Cat S. Thus, the CDR amino acid sequences in which one or more amino acid residues are modified may also be used as the CDR sequence. The modified amino acid residues in the amino acid sequences of the CDR variant are preferably 30% or less, more preferably 20% or less, most preferably 10% or less, within the entire CDR. Such variants may be provided using the teaching of the present application and techniques known in the art. The CDRs may be carried in a framework structure comprising an antibody heavy or light chain sequence or part thereof. Preferably such CDRs are positioned in a location corresponding to the position of the CDR(s) of naturally occurring VH and VL domains. The positions of such CDRs may be determined as described in Kabat et al, Sequences of Proteins of Immunological Interest, US Dept of Health and Human Services, Public Health Service, Nat'l Inst. of Health, NIH Publication No. 91-3242, 1991 and online at www.kabatdatabase.com http://immuno.bme.nwu.edu.

Furthermore, modifications may alternatively or additionally be made to the Framework Regions of the variable regions. Such changes in the framework regions may improve stability and reduce immunogenicity of the antibody.

The antibodies of our disclosure herein include "chimeric" antibodies in which a portion of the heavy and/or light chain is identical with or homologous to corresponding sequences in antibodies derived from a particular species or belonging to a particular antibody class or subclass, while. the remainder of the chain (s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81: 6851-6855 (1984)). Chimeric antibodies of interest herein include "primatized" antibodies comprising variable domain antigen-binding sequences derived from a non-human primate (e.g. Old World Monkey, Ape etc), and human constant region sequences.

Production of Specific Binding Members

Specific binding members of and for use our disclosure may be produced in any suitable way, either naturally or synthetically. Such methods may include, for example, traditional hybridoma techniques (Kohler and Milstein (1975) Nature, 256:495-499), recombinant DNA techniques (see e.g. U.S. Pat. No. 4,816,567), or phage display techniques using antibody libraries (see e.g. Clackson et al. (1991) Nature, 352: 624-628 and Marks et al. (1992) Bio/Technology, 10: 779-783). Other antibody production techniques are described in Antibodies: A Laboratory Manual, eds. Harlow et al., Cold Spring Harbor Laboratory, 1988.

Traditional hybridoma techniques typically involve the immunisation of a mouse or other animal with an antigen in order to elicit production of lymphocytes capable of binding the antigen. The lymphocytes are isolated and fused with a a myeloma cell line to form hybridoma cells which are then cultured in conditions which inhibit the growth of the parental myeloma cells but allow growth of the antibody producing cells. The hybridoma may be subject to genetic mutation, which may or may not alter the binding specificity of antibodies produced. Synthetic antibodies can be made using techniques known in the art (see, for example, Knappik et al, J. Mol. Biol. (2000) 296, 57-86 and Krebs et al, J. Immunol. Meth. (2001) 2154 67-84.

Modifications may be made in the VH, VL or CDRs of the binding members, or indeed in the FRs using any suitable technique known in the art. For example, variable VH and/or VL domains may be produced by introducing a CDR, e.g. CDR3 into a VH or VL domain lacking such a CDR. Marks et al. (1992) Bio/Technology, 10: 779-783 describe a shuffling technique in which a repertoire of VH variable domains lacking CDR3 is generated and is then combined with a CDR3 of a particular antibody to produce novel VH regions. Using analogous techniques, novel VH and VL domains comprising CDR derived sequences may be produced.

Accordingly, in one embodiment, we provide a method of generating a specific binding member having specificity for Cat S, the method comprising: (a) providing a starting repertoire of nucleic acids encoding a variable domain, wherein the variable domain includes a CDR1, CDR2 or CDR3 to be replaced or the nucleic acid lacks an encoding region for such a CDR; (b) combining the repertoire with a donor nucleic acid encoding an amino acid sequence having the sequence as shown as Seq ID No: 1, 2, 3, 4, 5 or 6 herein such that the donor nucleic acid is inserted into the CDR region in the repertoire so as to provide a product repertoire of nucleic acids encoding a variable domain; (c) expressing the nucleic acids of the product repertoire; (d) selecting a specific antigen-binding fragment specific for Cat S; and (e) recovering the specific antigen-binding fragment or nucleic acid encoding it. The method may include an optional step of testing the specific binding member for ability to inhibit the proteolytic activity of cathepsin S.

Alternative techniques of producing variant antibodies may involve random mutagenesis of gene(s) encoding the VH or VL domain using, for example, error prone PCR (see Gram et al, 1992, P.N.A.S. 89 3576-3580. Additionally or alternatively, CDRs may be targeted for mutagenesis e.g. using the molecular evolution approaches described by Barbas et al 1991 PNAS 3809-3813 and Scier 1996 J Mol Biol 263 551-567.

Having produced such variants, antibodies and fragments may be tested for binding to Cat S and for the ability to inhibit the proteolytic activity of cathepsin S.

As described herein, we have demonstrated that specific binding members have an anti-proteolytic effect. Furthermore anti invasive and anti-angiogenic activity has been demonstrated, as described in the Examples. This therefore enables the use of the specific binding members of our disclosure as active therapeutic agents. Accordingly in one embodiment of our disclosure, the specific binding member is a "naked" specific binding member. A "naked" specific binding member is a specific binding member which is not conjugated with an "active therapeutic agent".

In the context of the present application, an "active therapeutic agent" is a molecule or atom which is conjugated to a antibody moiety (including antibody fragments, CDRs etc) to produce a conjugate. Examples of such "active therapeutic agents" include drugs, toxins, radioisotopes, immunomodulators, chelators, boron compounds, dyes, nanoparticles etc.

In another embodiment of our disclosure, the specific binding member is in the form of an immunoconjugate, comprising an antibody fragment conjugated to an "active therapeutic agent".

Methods of producing immunoconjugates are well known in the art; for example, see U.S. Pat. No. 5,057,313, Shih et al., Int. J. Cancer 41: 832-839 (1988); Shih et al., Int. J. Cancer 46: 1101-1106 (1990), Wong, Chemistry Of Protein Conjugation And Cross-Linking (CRC Press 1991); Upeslacis et al., "Modification of Antibodies by Chemical Methods," in Monoclonal Antibodies: Principles And Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering And Clinical Application, Ritter et al. (eds.), pages 60-84 (Cambridge University Press 1995).

The specific binding members of our disclosure may comprise further modifications. For example the antibodies can be glycosylated, pegylated, or linked to albumin or a nonproteinaceous polymer. The specific binding member may be in the form of an immunoconjugate.

Antibodies of our disclosure may be labelled. Labels which may be used include radiolabels, enzyme labels such as horseradish peroxidase, alkaline phosphatase, or biotin.

The ability of a specific binding member to inhibit the proteolytic activity of cathepsin S may be tested using any suitable method. For example the ability of a specific binding member to inhibit the proteolytic activity of cathepsin S may be tested using a fluorimetric assay as detailed in the Examples. In such an assay, any suitable fluorigenic substrate may be used, for example Cbz-Val-Val-Arg-AMC as used in the Examples. A specific binding member is considered to inhibit the proteolytic activity of cathepsin S if it has the ability to inhibit its activity by a statistically significant amount. For example, in one embodiment, the specific binding member is able to inhibit the inhibitory activity by at least 10%, for example at least 10%, at least 20%, at least 30%, at least at least 40%, at least 50%, at least 60%, at least 70%, at least 80% or at least 90% when compared to an appropriate control antibody.

The ability of a specific binding member to inhibit tumour cell invasion may be tested using any suitable invasion assay known in the art. For example, such ability may be tested using a modified Boyden chamber as described in the Examples. The specific binding member may be tested using any suitable tumour cell line, for example a prostate carcinoma cell line, e.g. PC3, an astrocytoma cell line e.g. U251 mg, a colorectal carcinoma cell line, e.g. HCT116, or a breast cancer cell line, e.g. MDA-MB-231 or MCF7. A specific binding member is considered to inhibit tumour cell invasion if it has the ability to inhibit invasion by a statistically significant amount. For example, in one embodiment, the specific binding member is able to inhibit invasion by at least 10%, for example at least 25%, at least 50%, at least 60%, at least 70%, at least 80% or at least 90% when compared to an appropriate control antibody.

The ability of a specific binding member to inhibit angiogenesis may be tested using any suitable assay known in the art. For example, such ability may be tested using a Matrigel based assay as described in the Examples.

In one embodiment of our disclosure, a specific binding member for use in our disclosure may have inhibitory activity (for example to inhibit the proteolytic activity or invasion) with a potency of at least 25%, for example at least 40%, for example at least 50% of the inhibitory potency of an antibody comprising an antibody $V_H$ domain having the amino acid sequence Seq ID No: 7 and an antibody $V_L$ domain having the amino acid sequence Seq ID No: 8, when each is compared at its own $IC_{50}$.

Nucleic Acid

Nucleic acid of and for use in our disclosure may comprise DNA or RNA. It may be produced recombinantly, synthetically, or by any means available to those in the art, including cloning using standard techniques.

The nucleic acid may be inserted into any appropriate vector. A vector comprising a nucleic acid forms a further aspect of the disclosure. In one embodiment the vector is an expression vector and the nucleic acid is operably linked to a control sequence which is capable of providing expression of the nucleic acid in a host cell. A variety of vectors may be used. For example, suitable vectors may include viruses (e.g. vaccinia virus, adenovirus, etc.), baculovirus; yeast vectors, phage, chromosomes, artificial chromosomes, plasmids, or cosmid DNA.

The vectors may be used to introduce the nucleic acids into a host cell. A wide variety of host cells may be used for expression of the nucleic acid. Suitable host cells for use in our disclosure may be prokaryotic or eukaryotic. They include bacteria, e.g. *E. coli*, yeast, insect cells and mammalian cells. Mammalian cell lines which may be used include Chinese hamster ovary cells, baby hamster kidney cells, NSO mouse melanoma cells, monkey and human cell lines and derivatives thereof and many others.

A host cell strain that modulates the expression of, modifies, and/or specifically processes the gene product may be used. Such processing may involve glycosylation, ubiquitination, disulfide bond formation and general post-translational modification.

Accordingly, we also provide a host cell, which comprises one or more nucleic acid or vectors of our disclosure.

We also encompass a method of production of a specific binding member, the method comprising culturing a host cell comprising a nucleic acid under conditions in which expression of the nucleic specific binding members from the nucleic acid occurs and, optionally, isolating and/or purifying the specific binding member.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 5th ed., Ausubel et al. eds., John Wiley & Sons, 2005 and, Molecular Cloning: a Laboratory Manual: $3^{rd}$ edition Sambrook et al., Cold Spring Harbor Laboratory Press, 2001.

Treatment

The specific binding members and nucleic acids may be used in the treatment of a number of medical conditions.

Treatment" includes any regime that can benefit a human or non-human animal. The treatment may be in respect of an existing condition or may be prophylactic (preventative treatment). Treatment may include curative, alleviation or prophylactic effects.

The specific binding members and nucleic acids of our disclosure may be used in the treatment of a variety of condition and disorders. These include atherosclerosis and neoplastic disease, neurodegenerative disorders, autoimmune diseases, cancer, inflammatory disorders, asthma, and atherosclerosis, and pain.

Neurodegenerative disorders which may be treated using our binding members, nucleic acids and methods include, but are not limited to, Alzheimer's Disease, Multiple Sclerosis and Creutzfeldt—Jakob disease.

Autoimmune diseases for which our disclosure may be used include inflammatory muscle disease and rheumatoid arthritis.

Our binding members, nucleic acids and methods may also be used in the treatment of cancers.

"Treatment of cancer" includes treatment of conditions caused by cancerous growth and/or vascularisation and includes the treatment of neoplastic growths or tumours. Examples of tumours that can be treated using our disclosure are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, prostate, cervical and ovarian carcinoma, non-small cell lung cancer, hepatocellular carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, astrocytomas, gliomas and retinoblastomas.

Our disclosure may be particularly useful in the treatment of existing cancer and in the prevention of the recurrence of cancer after initial treatment or surgery.

Our specific binding members, nucleic acids and compositions may also be used in the treatment of other disorders mediated by or associated with angiogenesis. Such conditions include, for example, tumours, various autoimmune disorders, hereditary disorders, ocular disorders.

Our methods may be used to treat angiogenesis-mediated disorders including hemangioma, solid tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, peptic ulcer, *Helicobacter* related diseases, fractures, keloids, and vasculogenesis.

Specific disorders that can be treated, and compounds and compositions for use in the our methods, are described in more detail below.

Ocular Disorders Mediated by Angiogenesis

Various ocular disorders are mediated by angiogenesis, and may be treated using the methods described herein. One example of a disease mediated by angiogenesis is ocular neovascular disease, which is characterized by invasion of new blood vessels into the structures of the eye and is the most common cause of blindness. In age-related macular degeneration, the associated visual problems are caused by an ingrowth of choroidal capillaries through defects in Bruch's membrane with proliferation of fibrovascular tissue beneath the retinal pigment epithelium. In the most severe form of age-related macular degeneration (known as "wet" ARMD) abnormal angiogenesis occurs under the retina resulting in irreversible loss of vision. The loss of vision is due to scarring of the retina secondary to the bleeding from the new blood vessels. Current treatments for "wet" ARMD utilize laser based therapy to destroy offending blood vessels. However, this treatment is not ideal since the laser can permanently scar the overlying retina and the offending blood vessels often re-grow. An alternative treatment strategy for macular degeneration is the use of antiangiogenesis agents to inhibit the new blood vessel formation or angiogenesis which causes the most severe visual loss from macular degeneration.

Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, atopic keratitis, superior limbic keratitis, pterygium keratitis sicca, periphigoid radial keratotomy, and corneal graph rejection. Diseases associated with retinal/choroidal neovascularization include, but are not limited to, diabetic retinopathy, macular degeneration, presumed myopia, optic pits, chronic retinal detachment, hyperviscosity syndromes, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Thus, in an embodiment of our disclosure, our methods may be used in the treatment of angiogenesis-mediated ocular disorders, for example, macular degeneration.

Inflammation

Our specific binding members and methods may be used in the treatment of inflammation. By blocking the activity of Cat S, the specific binding members may prevent proper antigen presentation in 'inflammed' cells and thus dampen the inflammatory effects.

In such an embodiment, the antibody will ideally be taken into the cell to enter the lysosome. Thus targeting methods common in the art may be used. As shown in the Examples, from the pH binding experiments, we have demonstrated that the antibody will bind even at pH 4.9, suggesting that it may be effective in the lysosome.

Our methods may also be used to treat angiogenesis associated inflammation, including various forms of arthritis, such as rheumatoid arthritis and osteoarthritis.

Further, in these methods, treatment with combinations of the compounds described herein with other agents useful for treating the disorders is provided. Such agents include, for instance, cyclooxygenase-2 (COX-2) inhibitors, which are well known to those of skill in the art.

The blood vessels in the synovial lining of the joints can undergo angiogenesis. The endothelial cells form new vascular networks and release factors and reactive oxygen species that lead to pannus growth and cartilage destruction. These factors are believed to actively contribute to rheumatoid arthritis and also to osteoarthritis. Chondrocyte activation by angiogenic-related factors contributes to joint destruction, and also promotes new bone formation. The methods described herein can be used as a therapeutic intervention to prevent bone destruction and new bone formation.

Pathological angiogenesis is also believed to be involved with chronic inflammation. Examples of disorders that can be treated using the methods described herein include ulcerative colitis, Crohn's disease, bartonellosis, and atherosclerosis.

Pharmaceutical Compositions

The binding members and nucleic acids may be administered as a pharmaceutical composition. Pharmaceutical compositions and for use in accordance with our disclosure may comprise, in addition to active ingredients, a pharmaceutically acceptable excipient, a carrier, buffer stabiliser or other materials well known to those skilled in the art (see, for example, (Remington: the Science and Practice of Pharmacy, $21^{st}$ edition, Gennaro A R, et al, eds., Lippincott Williams & Wilkins, 2005.). Such materials may include buffers such as acetate, Tris, phosphate, citrate, and other organic acids; antioxidants; preservatives; proteins, such as serum albumin, gelatin, or immunoglobulins; hydrophilic polymers such as polyvinylpyrrolidone; amino acids such as glycine, glutamine, asparagine, histidine, arginine, or lysine; carbohydrates; chelating agents; tonicifiers; and surfactants.

The pharmaceutical compositions may also contain one or more further active compound selected as necessary for the particular indication being treated, preferably with complementary activities that do not adversely affect the activity of our binding member, nucleic acid or composition. For example, in the treatment of cancer, in addition to an anti Cat S specific binding member of our disclosure, the formulation may comprise an additional antibody which binds a different epitope on Cat S, or an antibody to some other target such as a growth factor that e.g. affects the growth of the particular cancer, and/or a chemotherapeutic agent.

The active ingredients (e.g. specific binding members and/or chemotherapeutic agents) may be administered via microspheres, microcapsules liposomes, other microparticulate delivery systems. For example, active ingredients may be entrapped within microcapsules which may be prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. For further details, see Remington: the Science and Practice of Pharmacy, $21^{st}$ edition, Gennaro A R, et al, eds., Lippincott Williams & Wilkins, 2005.

Sustained-release preparations may be used for delivery of active agents. Suitable examples of sustained-release preparations include semi-permeable matrices of solid hydrophobic polymers containing the antibody, which matrices are in the form of shaped articles, e.g. films, suppositories or microcapsules. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid andy ethyl-Lglutamate, non-degradable ethylene-vinyl acetate, degradable lactic acid-glycolic acid copolymers, and poly-D-(−)-3-hydroxybutyric acid.

As described above, nucleic acids of our disclosure may also be used in methods of treatment. Nucleic acid of our disclosure may be delivered to cells of interest using any suitable technique known in the art. Nucleic acid (optionally contained in a vector) may be delivered to a patient's cells using in vivo or ex vivo techniques. For in vivo techniques, transfection with viral vectors (such as adenovirus, Herpes simplex I virus, or adeno-associated virus) and lipid-based systems (useful lipids for lipid-mediated transfer of the gene are DOTMA, DOPE and DC-Chol, for example) may be used (see for example, Anderson et al., Science 256: 808-813 (1992). See also WO 93/25673).

In ex vivo techniques, the nucleic acid is introduced into isolated cells of the patient with the modified cells being administered to the patient either directly or, for example, encapsulated within porous membranes which are implanted into the patient (see, e.g. U.S. Pat. Nos. 4,892,538 and 5,283,187). Techniques available for introducing nucleic acids into viable cells may include the use of retroviral vectors, liposomes, electroporation, microinjection, cell fusion, DEAE-dextran, the calcium phosphate precipitation method, etc.

The binding member, agent, product or composition may be administered in a localised manner to a tumour site or other desired site or may be delivered in a manner in which it targets tumour or other cells. Targeting therapies may be used to deliver the active agents more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Dose

Our binding members, nucleic acids or compositions are preferably administered to an individual in a "therapeutically effective amount", this being sufficient to show benefit to the individual. The actual dosage regimen will depend on a number of factors including the condition being treated, its severity, the patient being treated, the agent being used, and will be at the discretion of the physician.

The optimal dose can be determined by physicians based on a number of parameters including, for example, age, sex, weight, severity of the condition being treated, the active ingredient being administered and the route of administration.

As a rough guideline, doses of antibodies may be given in amounts of 1 ng/kg-500 mg/kg of patient weight.

Our disclosure will now be described further in the following non-limiting examples. Reference is made to the accompanying drawings in which.

Figure 2:
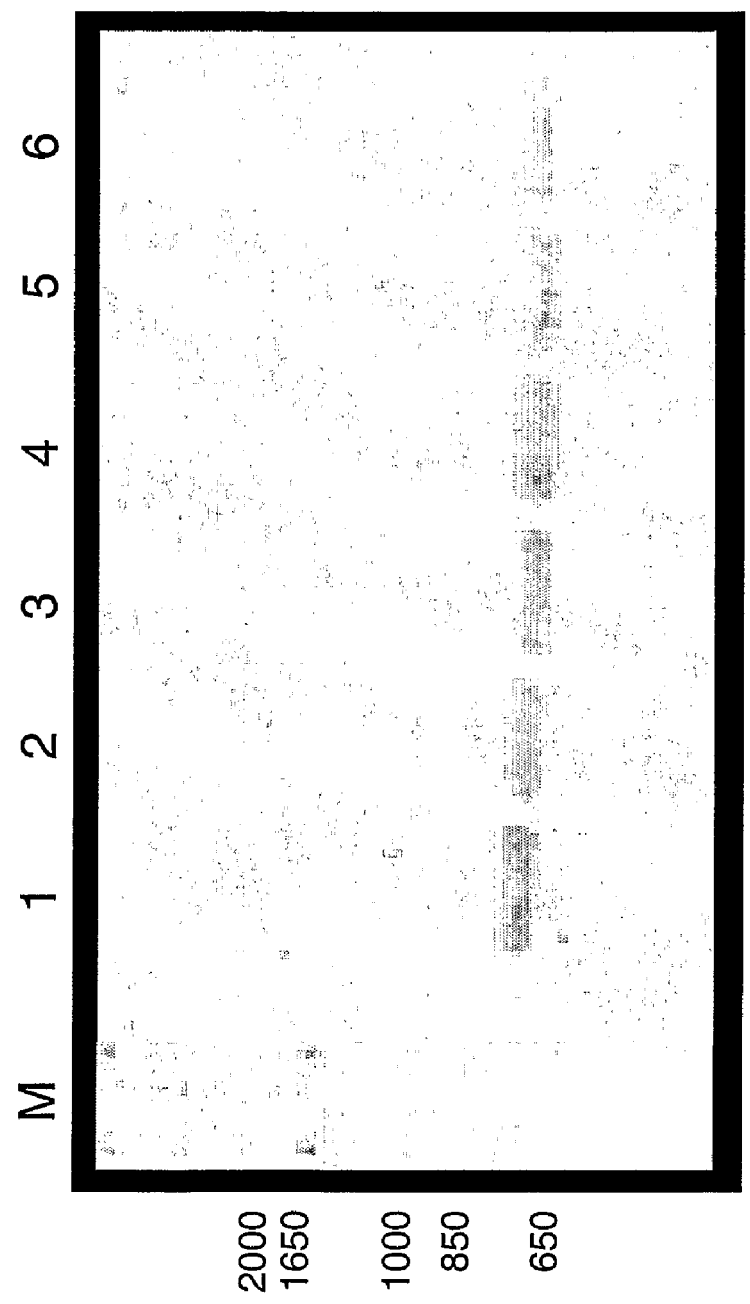
FIG. 2 illustrates colony PCR of 6 clones (lanes 1-6) containing the gene specific region of mature Cat S protein cloned into the bacterial expression vector pQE30. These demonstrate that the cloning has been successful in all six colonies selected.
Figure 3:
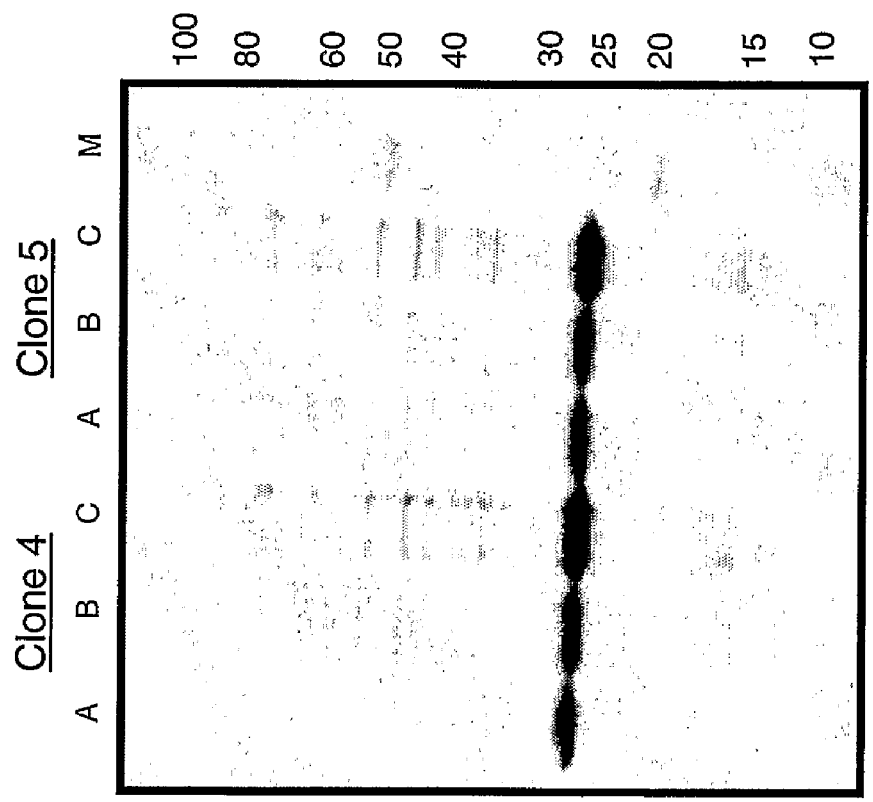

FIG. 3 illustrates scouting for optimal induction of protein expression from clones 4 and 5 (from FIG. 2). Expression was induced using IPTG when cultures had OD values of 0.2 (early), 0.5 (mid) and 0.7 (late) OD 550 nm (A-C respectively). Bacterial protein lysates were analysed by gel electrophoresis and the gel stained with Coomassie brilliant blue stain.

Figure 4:
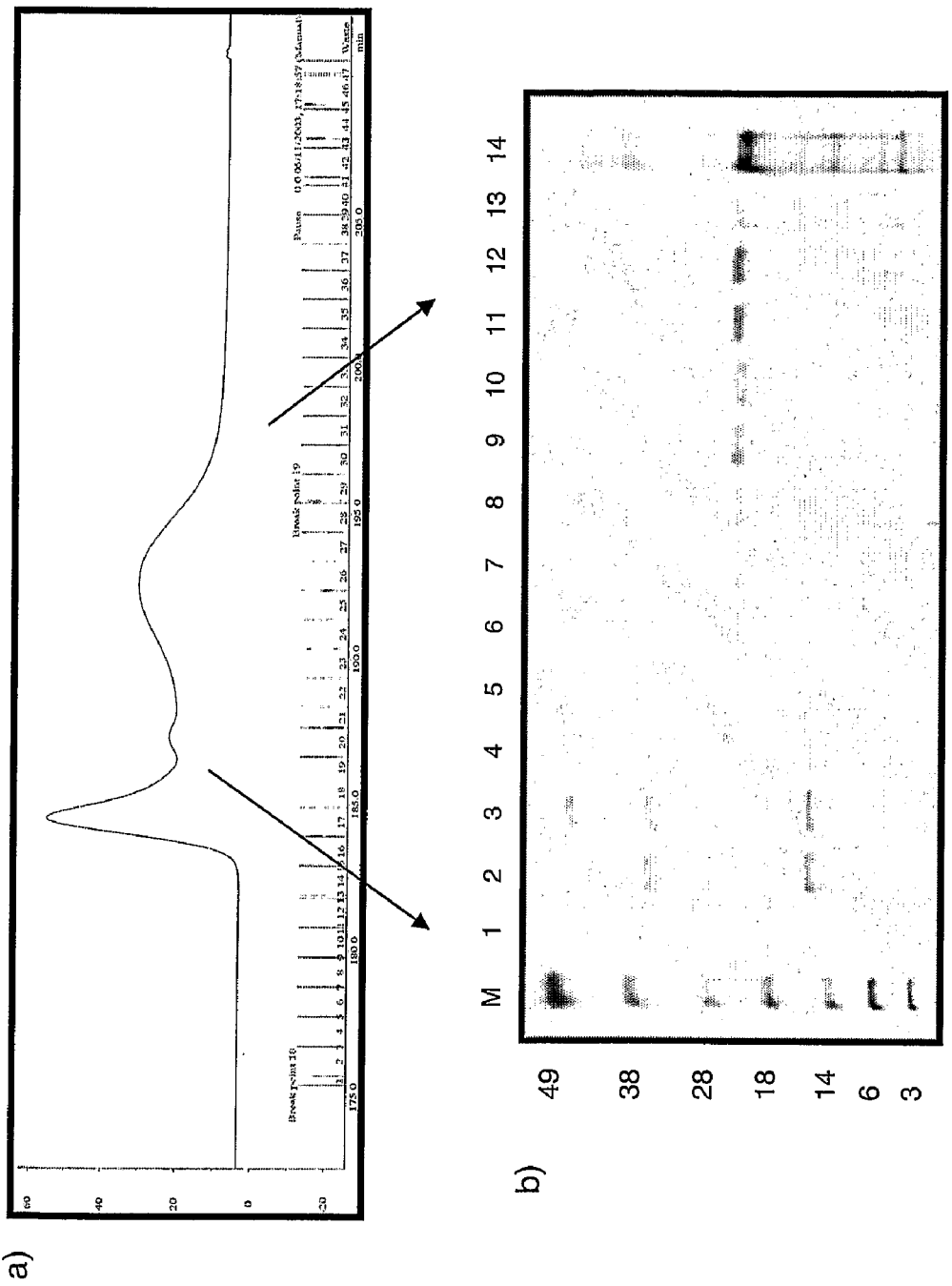

FIG. 4 illustrates purification of Cat S protein by immobilised metal affinity chromatography. a) Purification profile monitoring protein absorbance at 260 nm, showing elution of non-specific proteins from the column in the first peak, with elution of the Cat S recombinant protein seen in the broader second peak.

b) Protein elution fractions were analysed by SDS-PAGE. Lanes 1-13 are fractions eluted from the column during purification. Lane 14 is a crude bacterial lysate sample, not subjected to purification. Isolation of the Cat S recombinant protein to a high purify can be clearly seen in fractions 6-12.

Figure 5:
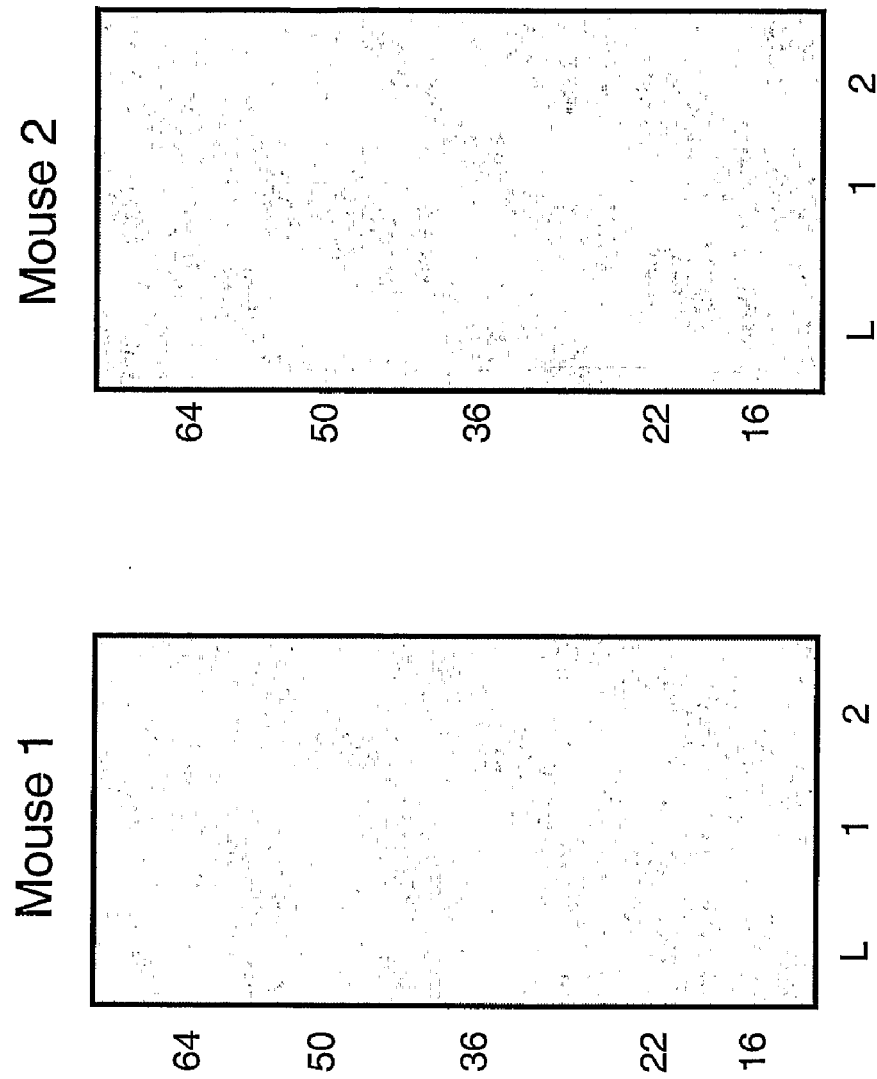

FIG. 5 illustrates analysis of test-bleeds by western blotting using a non-related recombinant protein (1) and the Cat S recombinant protein (2). Specific binding of murine sera was disclosed using goat anti-mouse HRP.

FIG. 6. ELISA screening of the hybridoma supernatants. Ag+denotes wells coated with the Cat S recombinant protein whereas Ag—denotes coating with an unrelated recombinant protein as a negative control. The hybridoma supernatants have all shown a high specificity for the Cat S recombinant protein, whilst little or no specificity for the control protein antigen.

Figure 7:
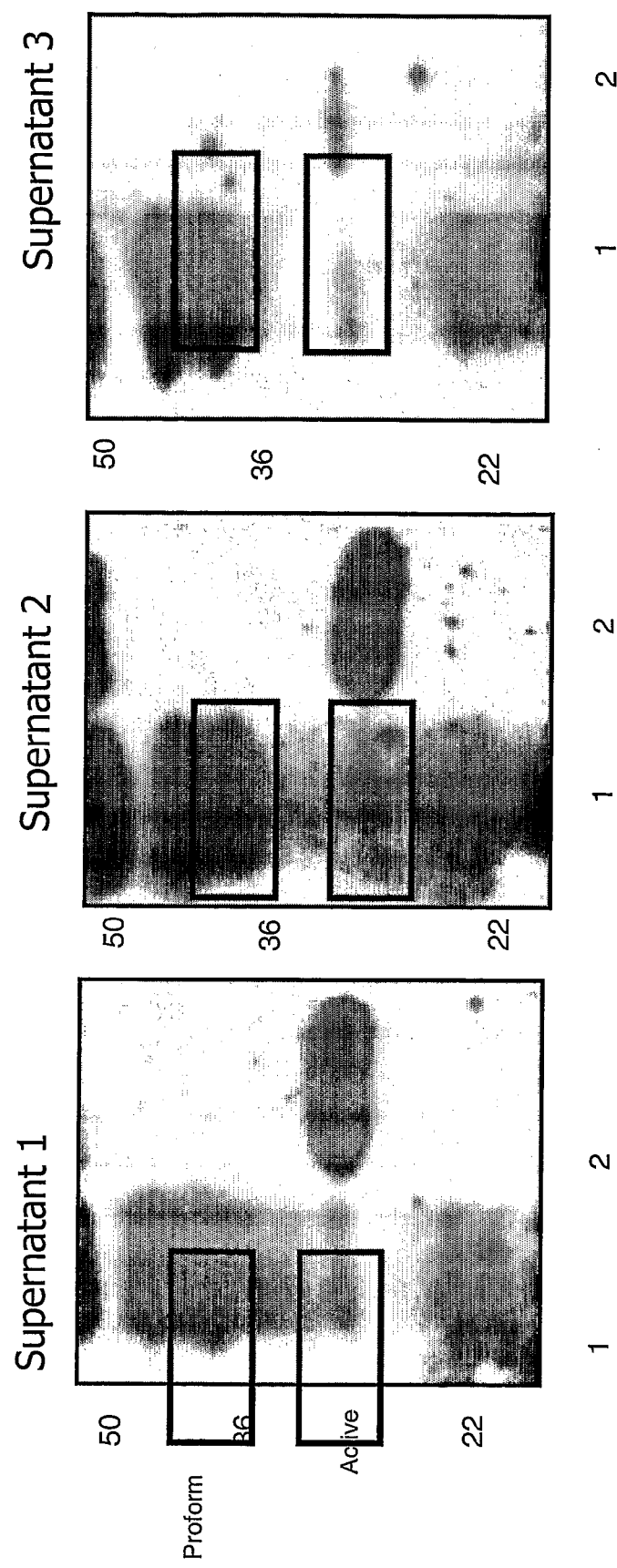

FIG. 7 illustrates hybridoma supernatants analysed by western blotting against endogenous Cat S protein from the U251 grade IV astrocytoma cell line (1) and the recombinant protein (2). Each of the unpurified supernatants analysed show the ability to recognise both the inactive pro-form of Cat S and the mature form from the U251 mg cell line within which Cat S has previously been shown to be highly expressed (as highlighted by the boxes).

Figure 8:
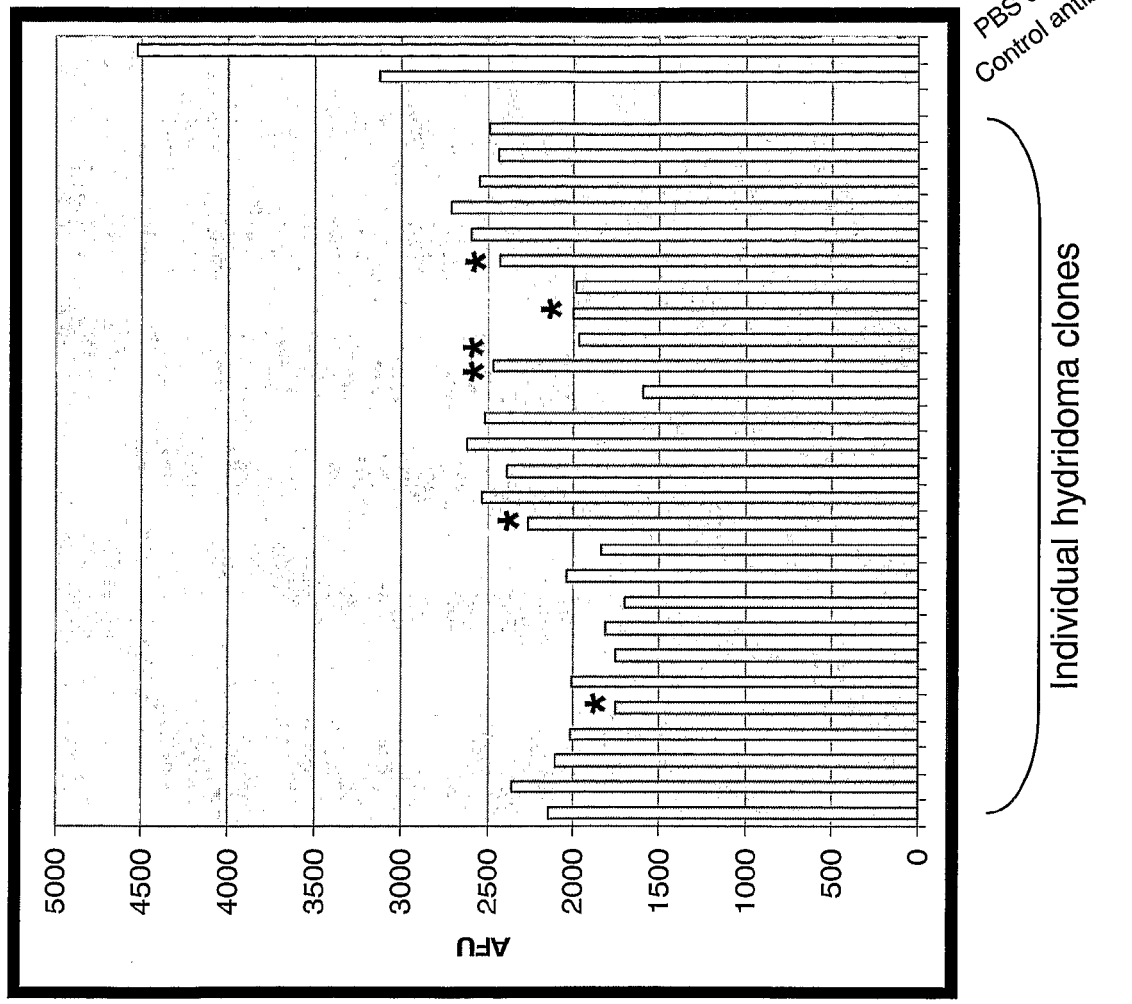

FIG. 8 Screening of hydridoma supernatants for antibodies which can inhibit Cat S-mediated hydrolysis of the fluorogenic substrate Cbz-Val-Val-Arg-AMC. Asterisk labelled columns represent the hydridoma clones taken forward for further examination. Some of the most inhibitory clones were not able to be propagated further and therefore were not chosen. The double asterisked clone represents the final selected inhibitory antibody.

Figure 9:
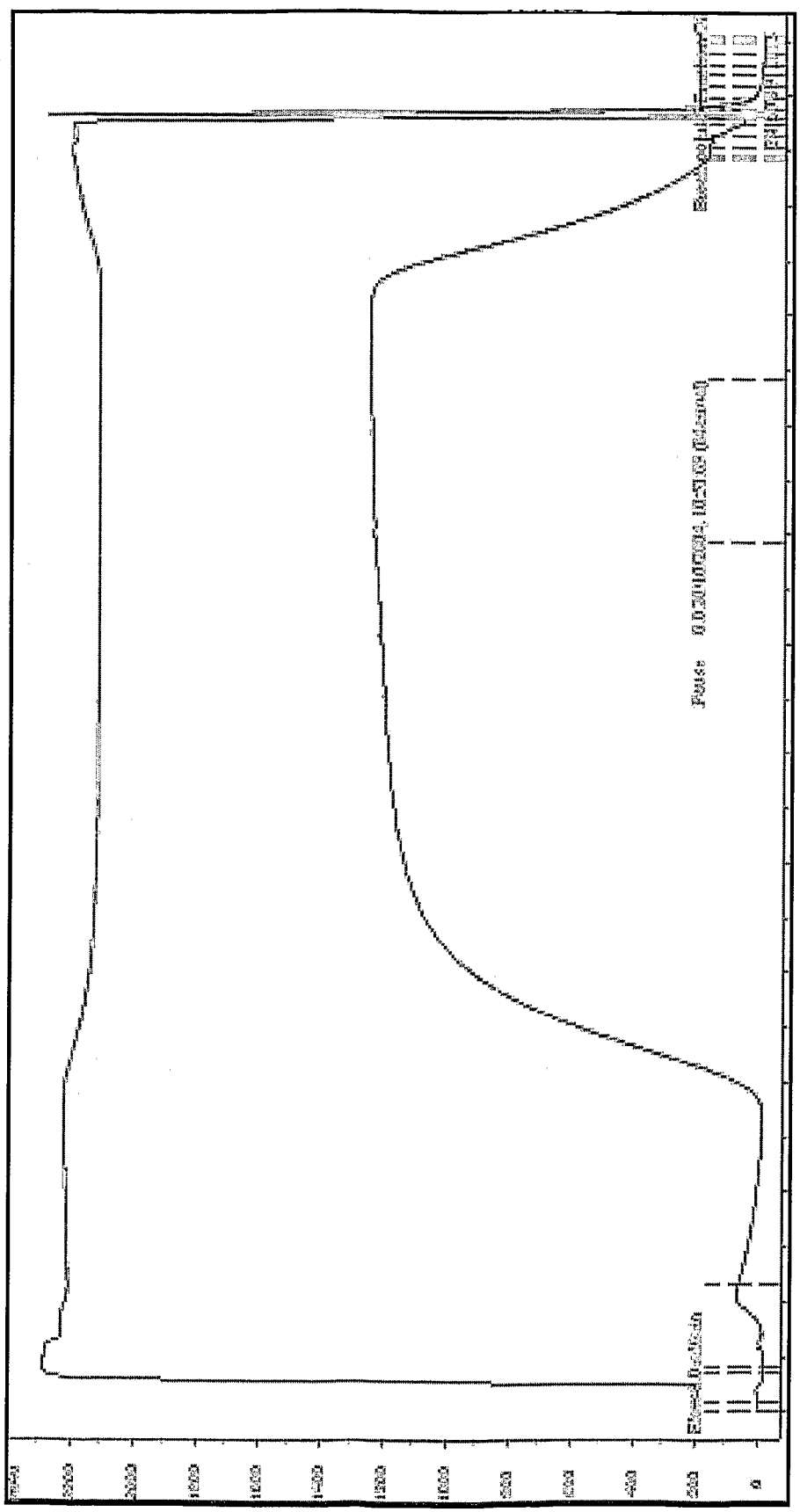

FIG. 9 illustrates representative elution profile of Cat S specific monoclonal antibodies. The lower trace represents absorbance (260 nm) with purification of the monoclonal antibody. The peak on the right indicates the elution of the monoclonal antibody and the bars below represent which fractions contain the eluted antibody.

FIG. 10 illustrates results from the isotyping of the monoclonal antibodies. Values greater than 0.8 and highlighted in bold are positive. Four of the antibodies tested were IgG1 antibodies with two being IgM and all six antibodies have kappa light chains. Ab 1, labelled with the asterisk represents the antibody finally identified as an inhibitory antibody. Antibody 2 is Cat S specific, but non-inhibitory, and is used in the later invasion assays as the isotype control.

Figure 11:
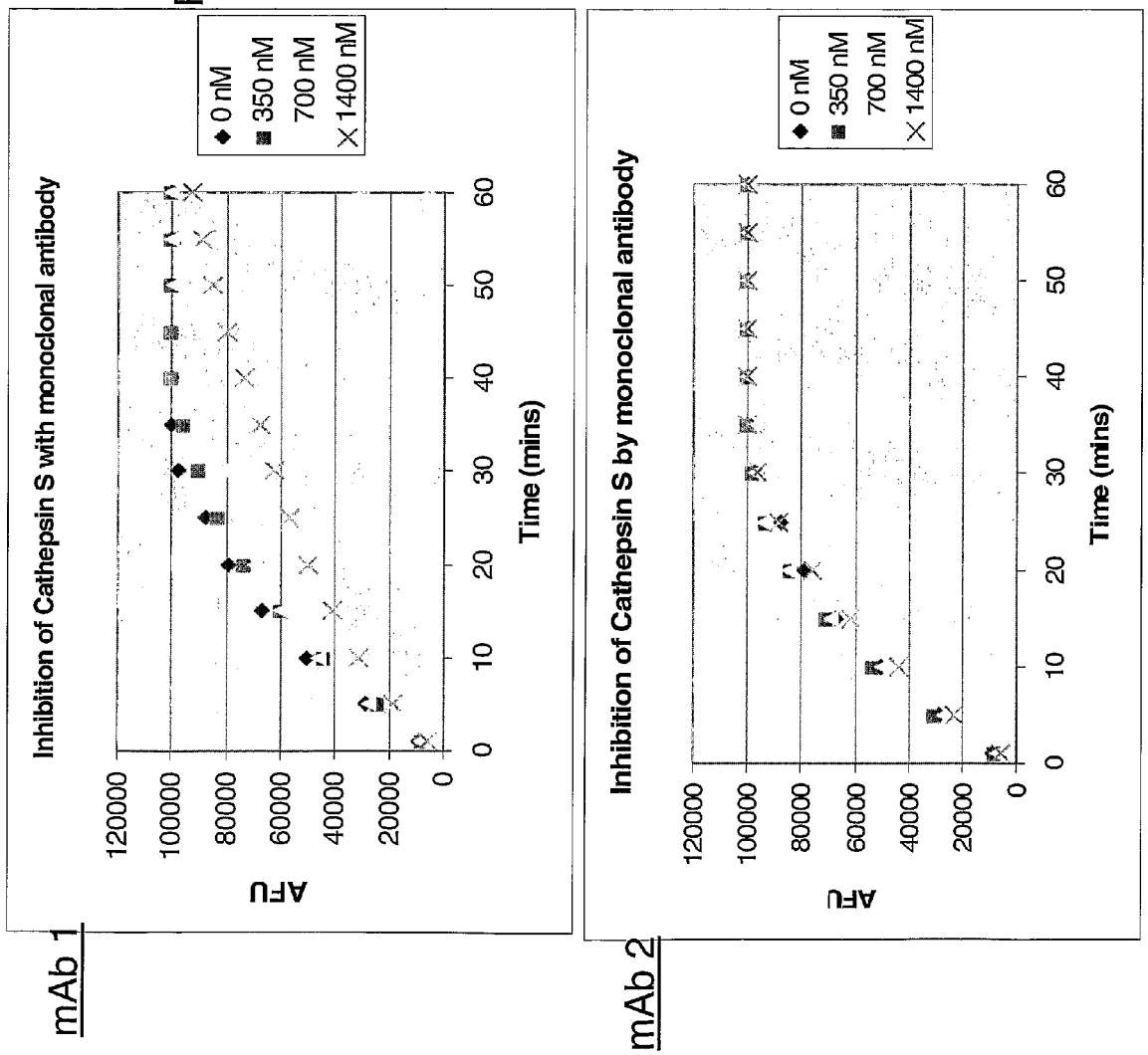

FIG. 11 illustrates fluorometric assays demonstrating inhibition of Cat S activity in the presence of varying concentrations of two purified Cat S MAb antibodies. MAb1 shows dose-dependent inhibition of Cbz-Val-Val-Arg-AMC cleavage by Cat S. MAb2 in this panel does not have any effect on proteolytic activity of Cat S.

Figure 12:
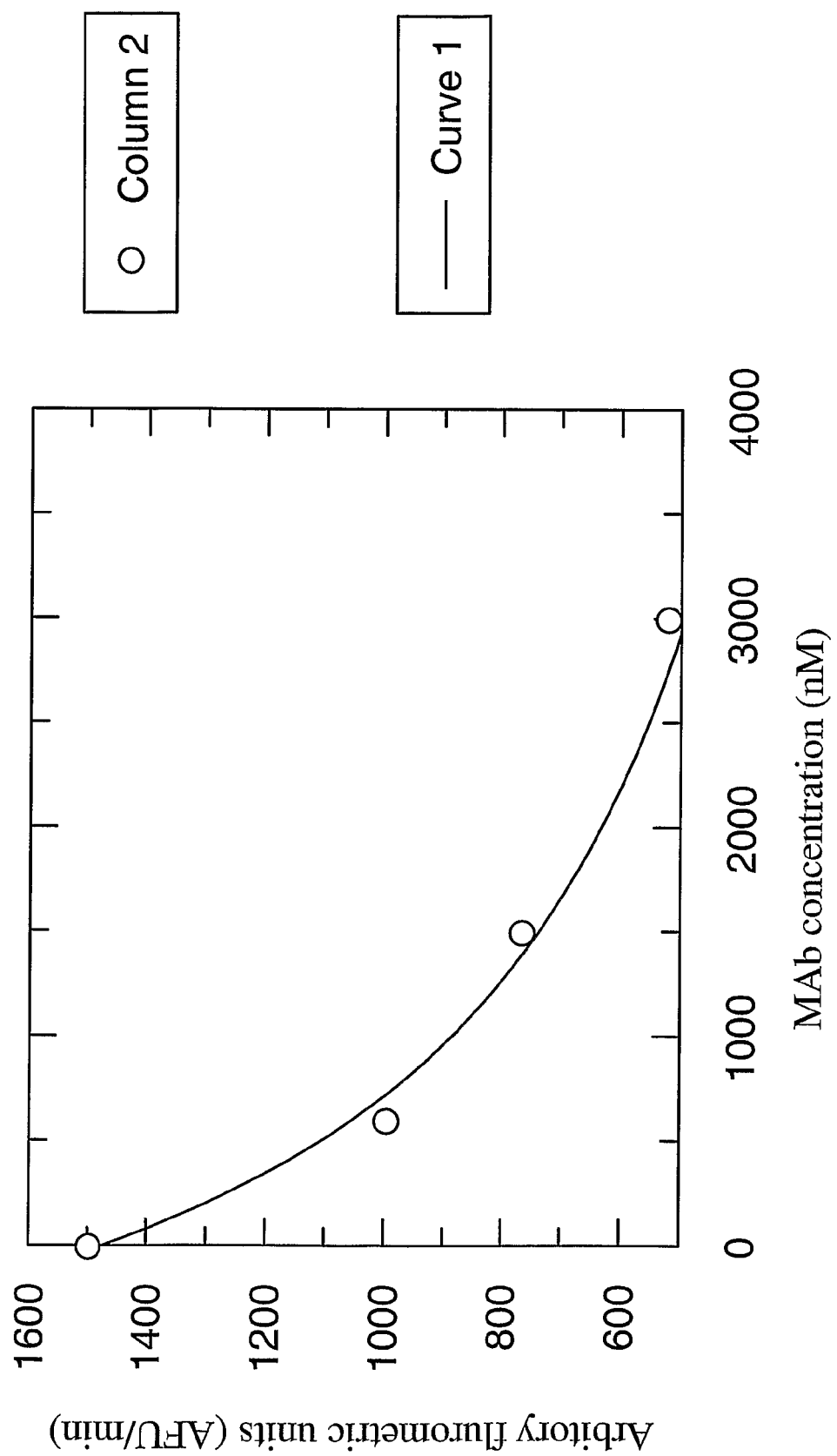

FIG. 12. Quantification of inhibitory activity of Cat S MAb1 (Mab 1E11). Rates from the progress curves of (Mab 1E11) [FIG. 11], which were indicative of a slow binding inhibitor, were fitted by non-linear regression using GraFit software according to the method of Morrison and Walsh, 1988. Using this approach an inhibition constant ($K_i$) of 533 nM was calculated.

Figure 13:
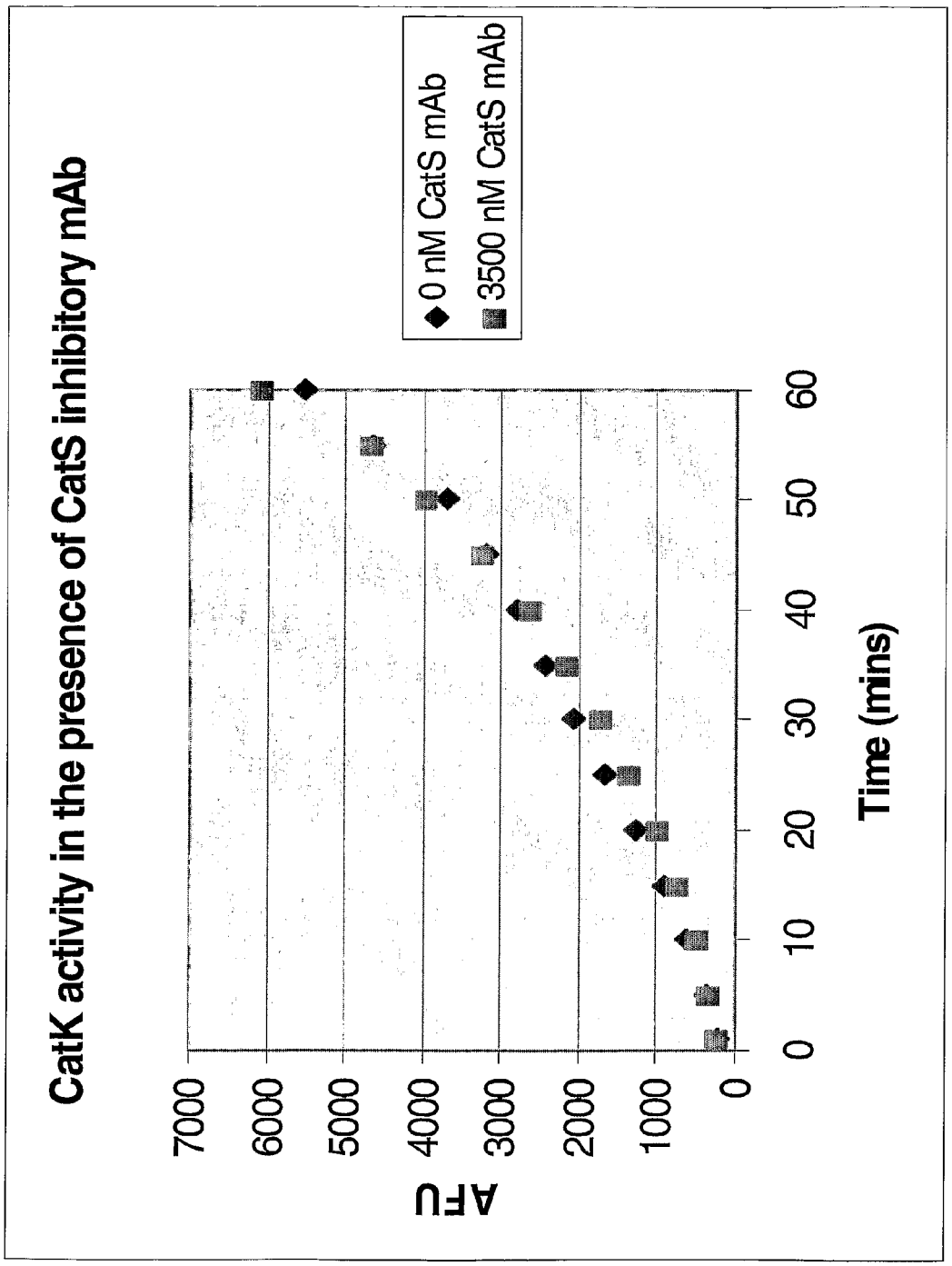

FIG. 13. MAb1 does not inhibit CatK. Progression curves plotted showing hydrolysis of Cbz-Phe-Arg-AMC by purified CatK in the presence of the Cat S inhibitory mAb.

Figure 14:
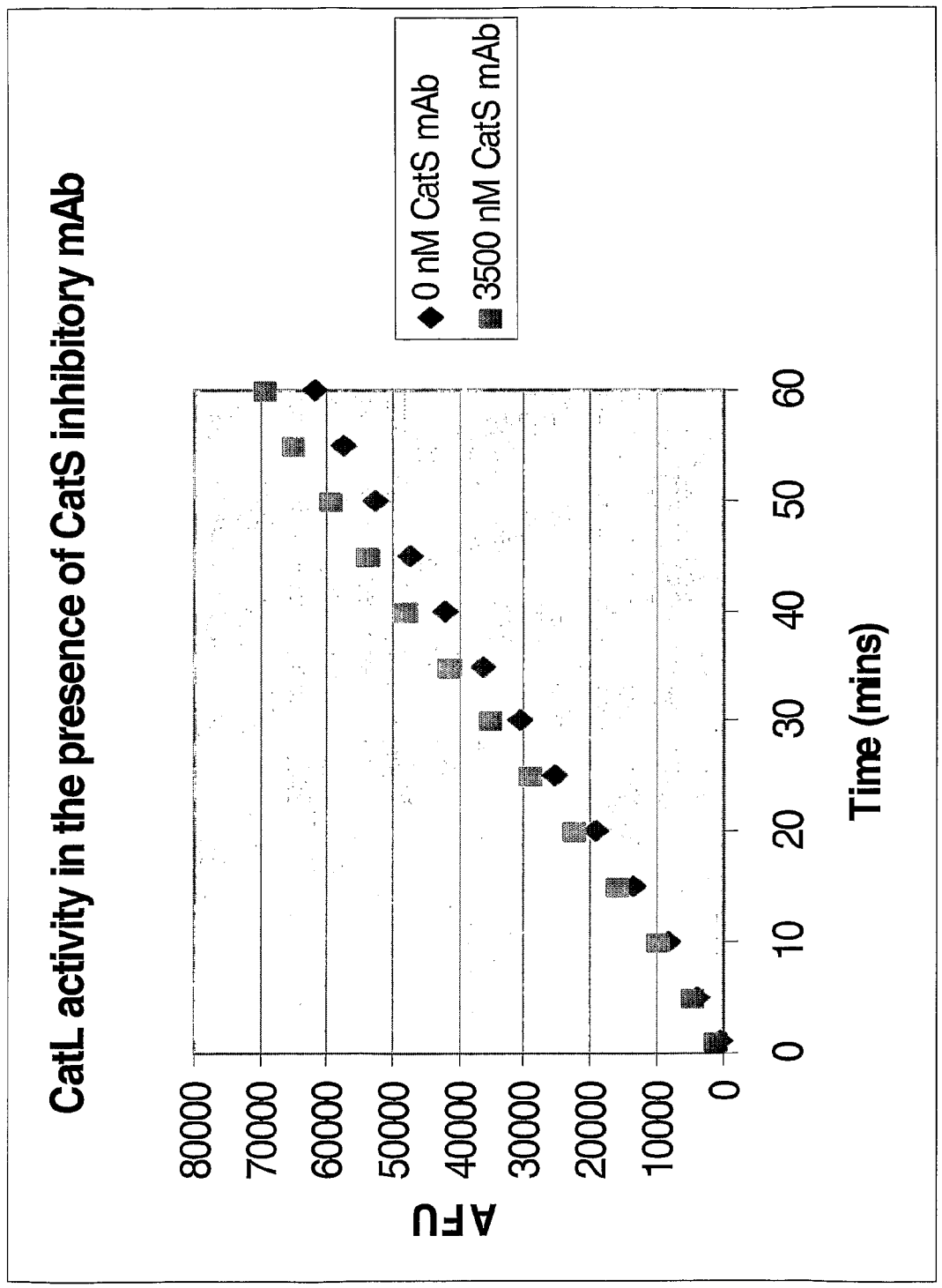

FIG. 14 MAb1 does not inhibit CatL. Progression curves plotted showing hydrolysis of Cbz-Phe-Arg-AMC by purified CatL in the presence of the Cat S inhibitory mAb.

Figure 15:
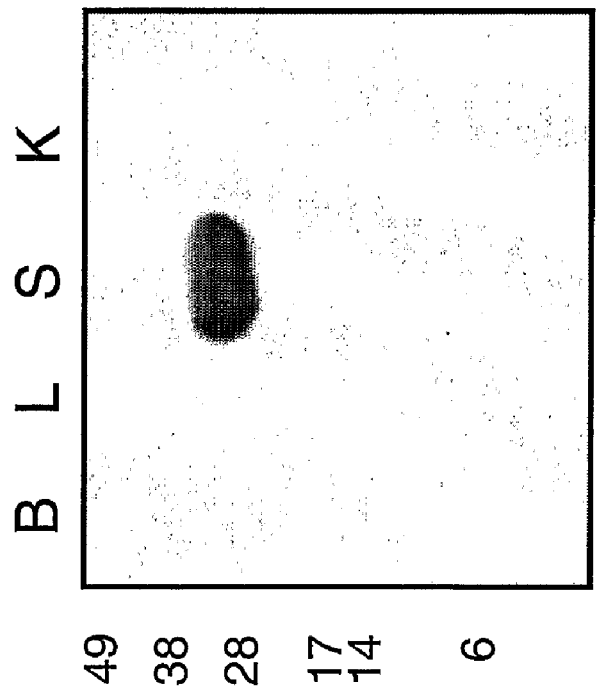

FIG. 15 MAb1 specifically binds Cat S on western blot. The antibody was used to probe against human cathepsin B, L, S and K (100 ng each).

Figure 16:
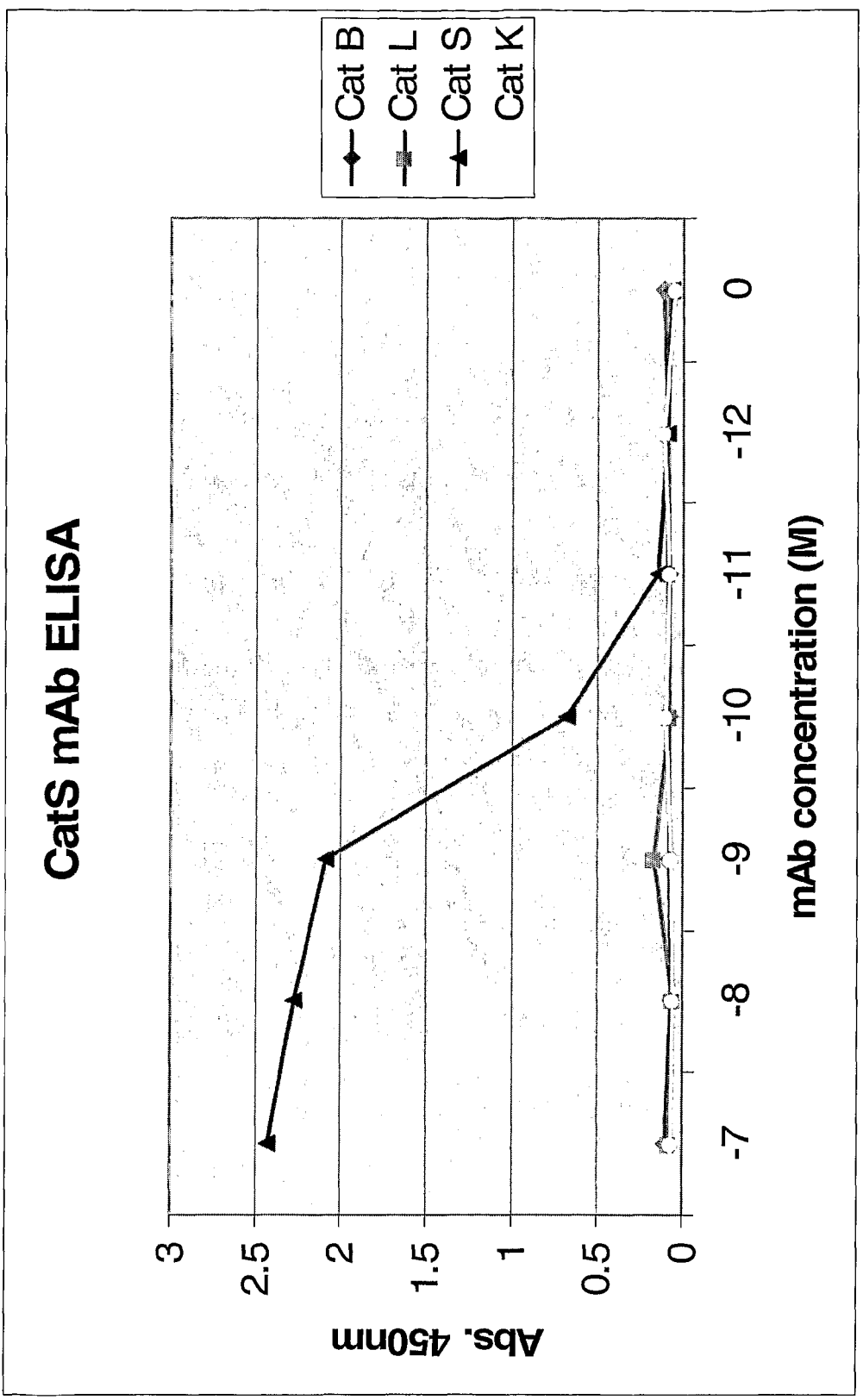

FIG. 16 Cat S Mab 1 binds specifically to Cat S by ELISA. Graph demonstrates results of antigen immobilised ELISA performed with Cat S, B, L and K recombinant proteins (100 ng per well) to which the Cat S inhibitory antibody was incubated in a range of dilutions, from $1 \times 10^{-7}$ to $1 \times 10^{-12}$M.

Figure 17:
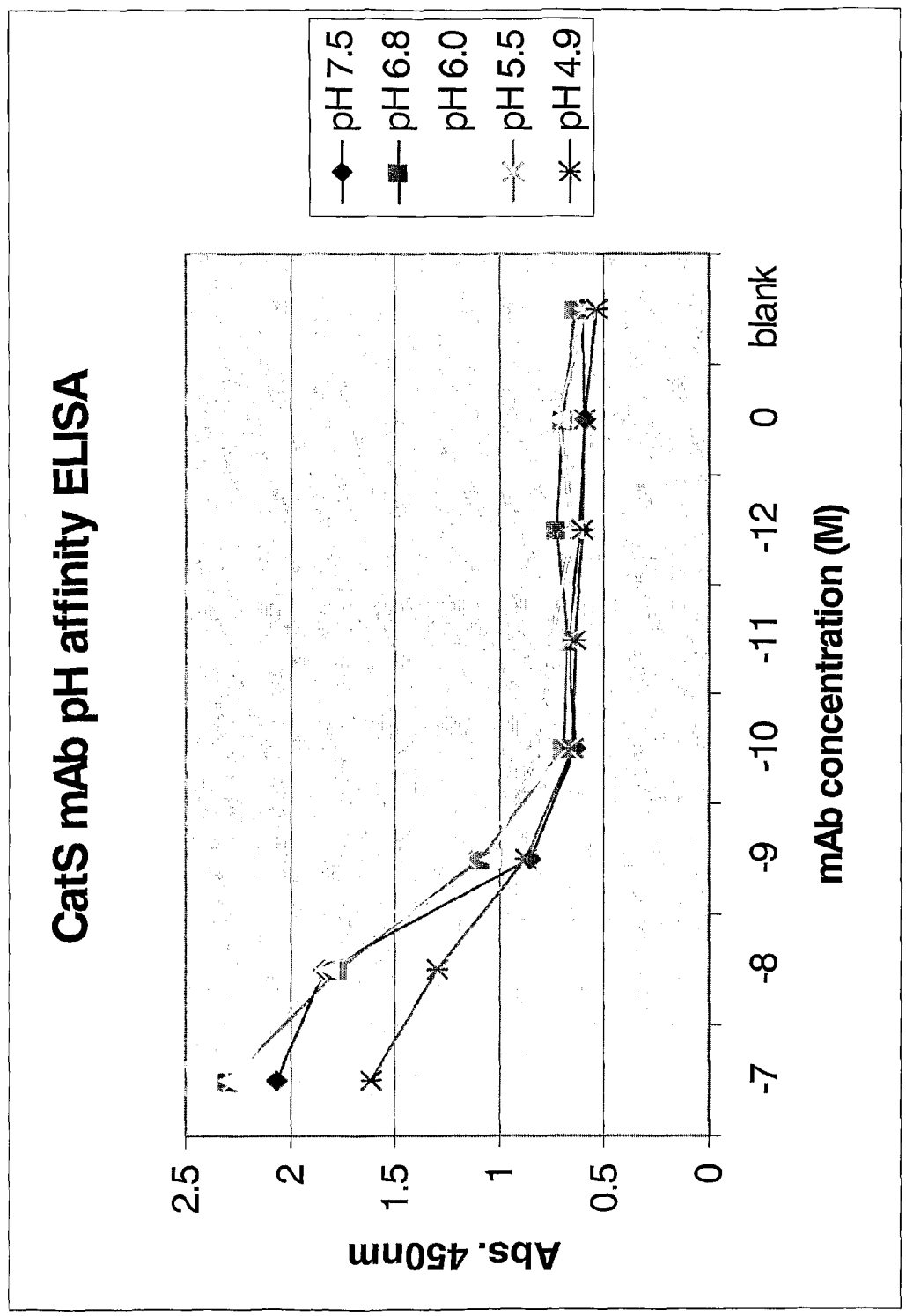

FIG. 17 Cat S MAb1 binds to Cat S over pH range. Graph shows results of an immobilised antigen ELISA showing the ability of different concentrations of the Cat S inhibitory antibody to maintain its affinity for Cat S over a wide pH range; from neutral pH 7.5 to pH 4.9.

Figure 18:
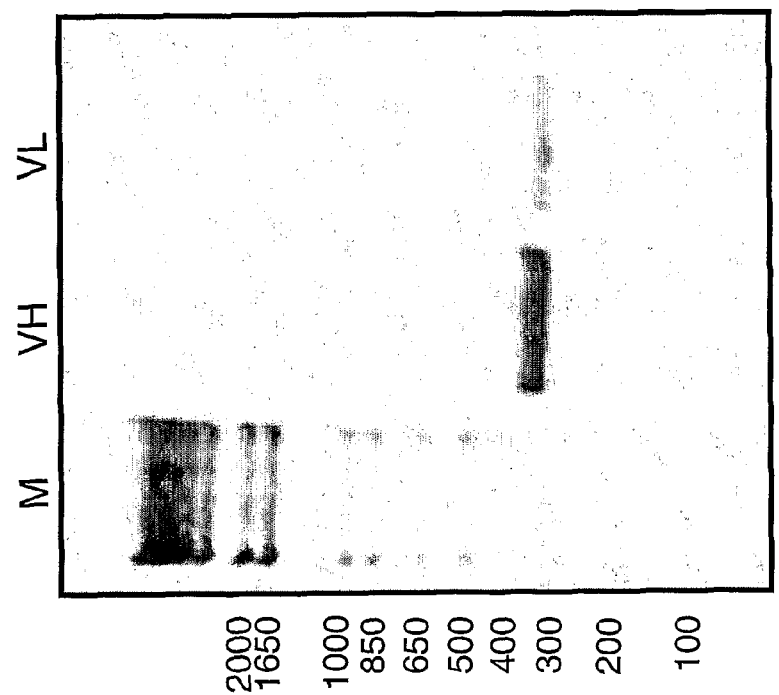

FIG. 18 illustrates the RT-PCR amplification of variable region of the heavy chain (HV) and the variable region of the light chain (LV) and VL regions of the inhibitory monoclonal antibody. The RT-PCR was performed from mRNA isolated from the hydridoma expressing and secreting Cat S MAb1.

Figure 19:
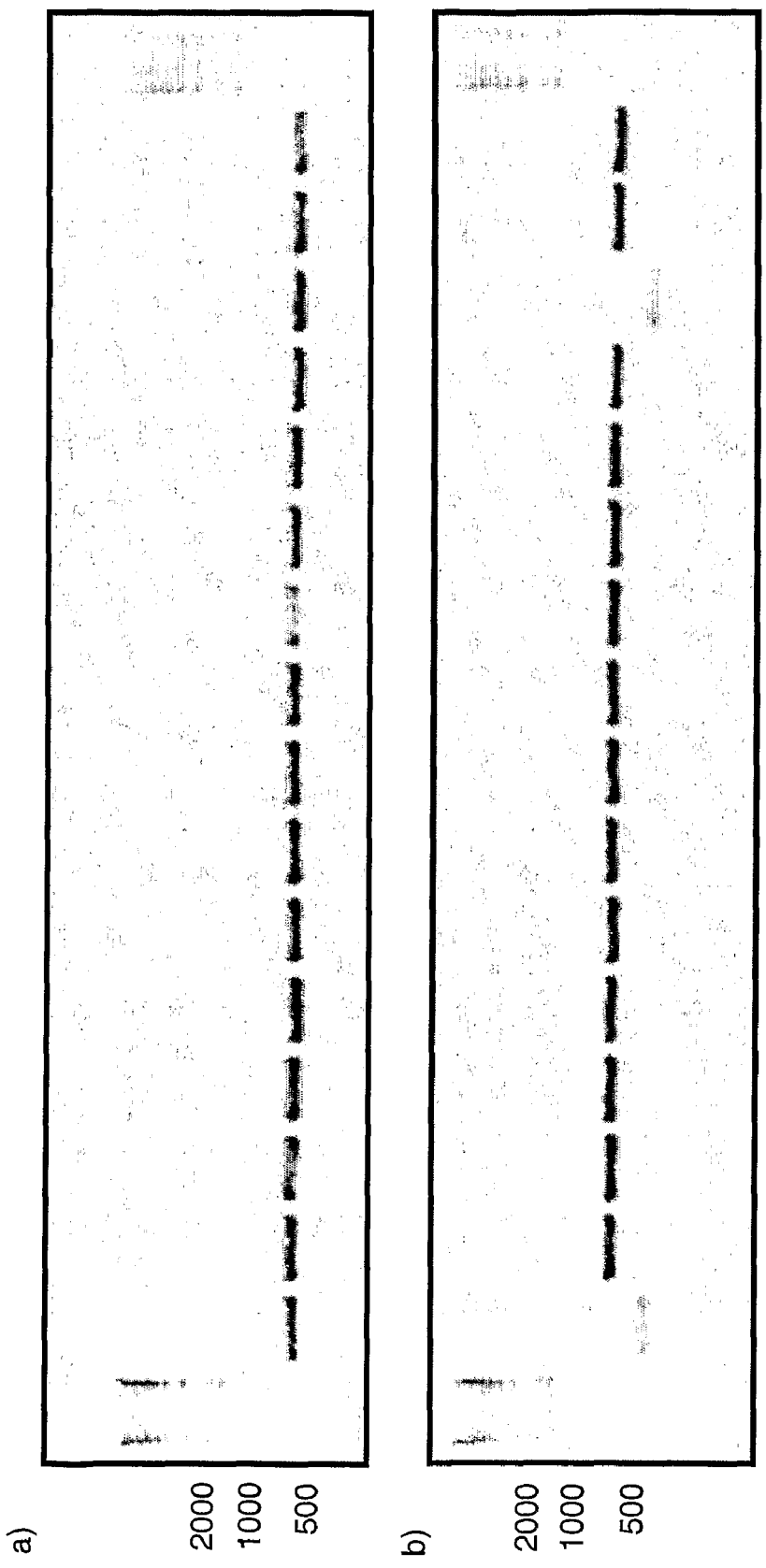

FIG. 19 illustrates the results from the colony PCR on the TOPO cloning of (a) VH and (b) VL. All 16 colonies analysed for the VH region appear positive by colony PCR, and all but two are positive for the VL region.

FIG. 20 illustrates the consensus amino acid sequence of the VH (SEQ ID NO: 7) and VL (SEQ ID NO: 8) regions of the inhibitory monoclonal antibody with CDR's CDRs highlighted in bold and underlined, as determined from DNA sequencing of the VH and VL regions.

Figure 21:
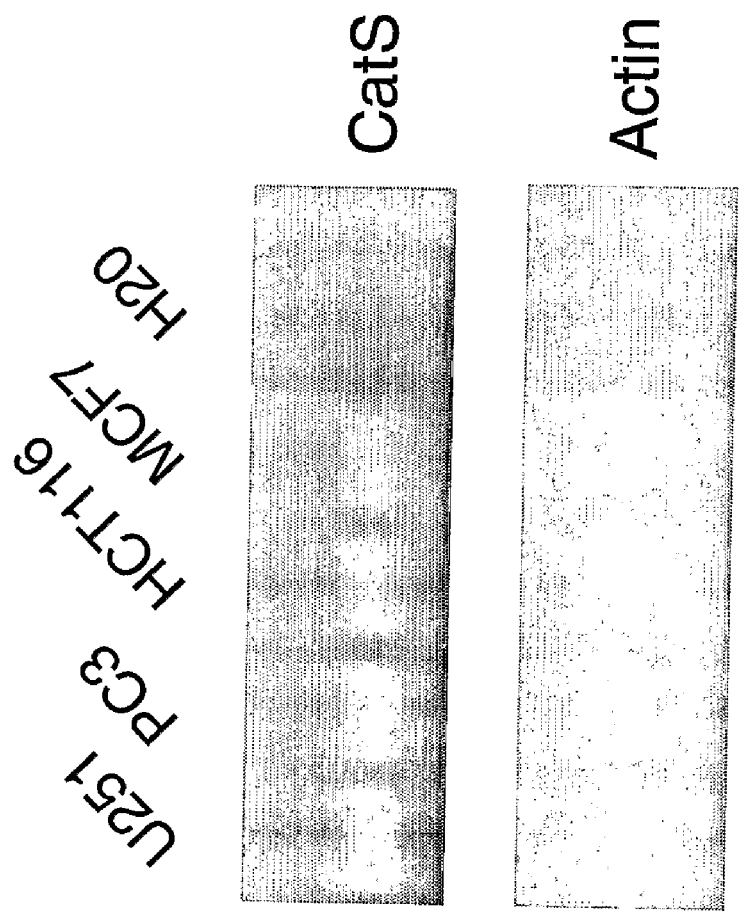

FIG. 21 RT-PCR of Cat S to identify expression in a range of tumour cell lines, grade IV astrocytoma (U251), prostate (PC3), colorectal (HCT116) and breast (MCF7).

Figure 22:
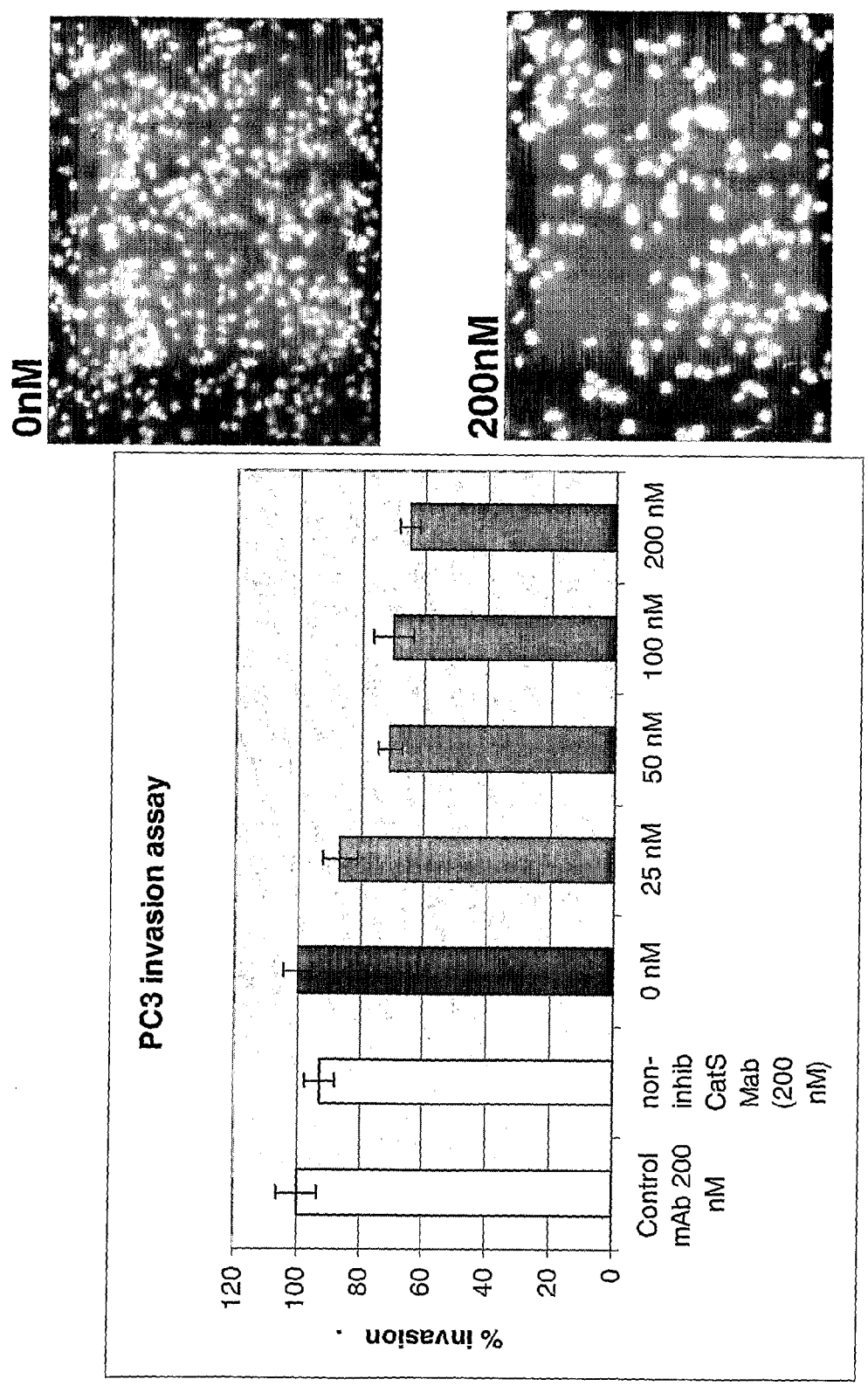

FIG. 22 shows the effect of the Cat S inhibitory monoclonal antibody in an in vitro invasion assay on the PC3 prostate carcinoma cell line. The invasion assay was performed in the presence of increasing concentrations of the inhibitory antibody (0-200 nM), showing a reduction in tumour cell invasion of up to 39%. A non-related isotype control mAb had no effect on invasion, while another Cat S mAb (which we have previously shown could bind to but not inhibit the proteolytic activity of Cat S) had no significant effect on invasion at 200 nM. Representative photomicrographs are also shown.

Figure 23:
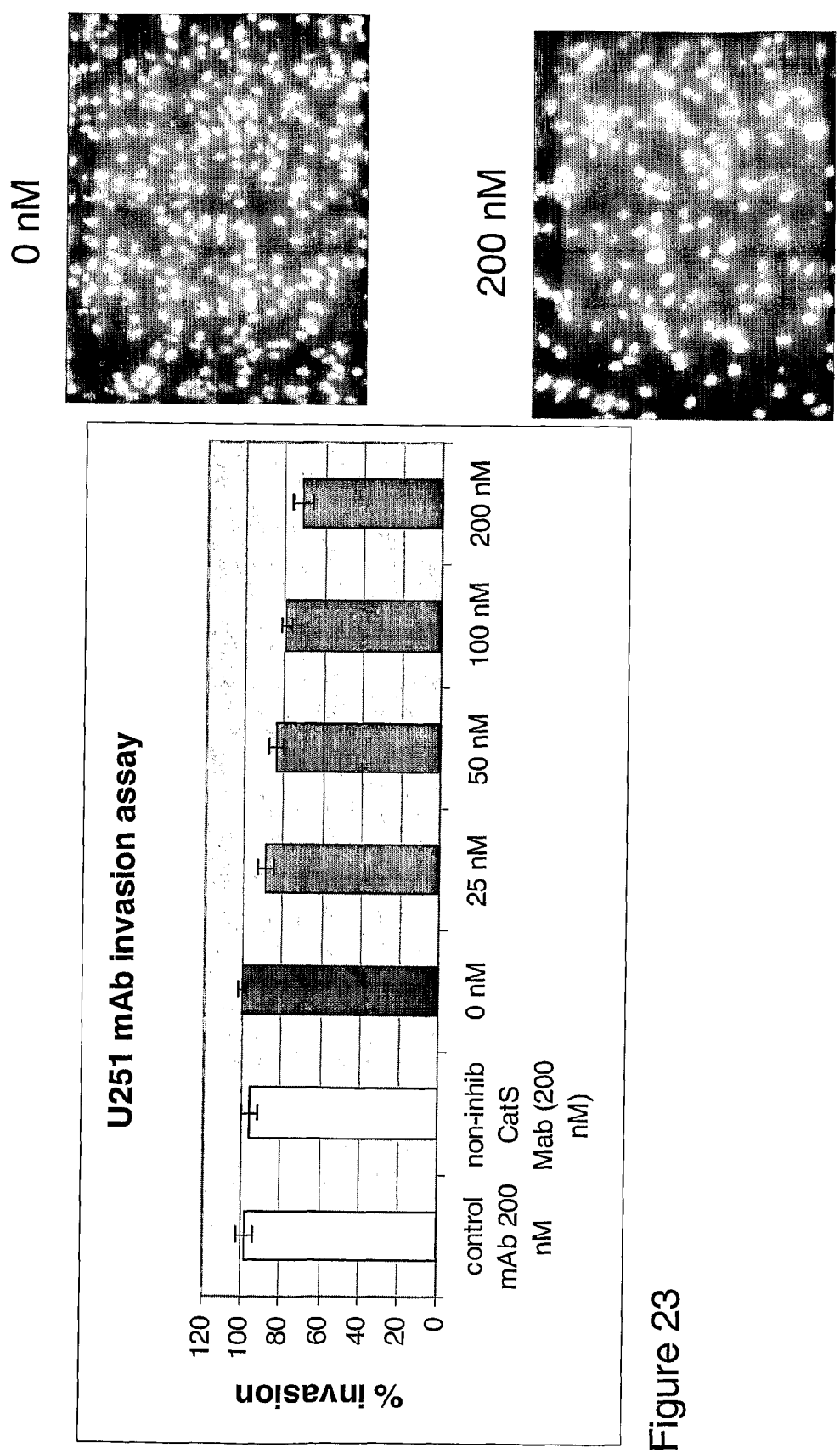

FIG. 23 illustrates the effect of the Cat S inhibitory monoclonal antibody in an in vitro invasion assay on the U251 mg astrocytoma cell line. The invasion assay was performed in the presence of increasing concentrations of the inhibitory antibody (0-200 nM), showing a reduction in tumour cell invasion of up to 29%. A non-related isotype control mAb and a non-inhibitory Cat S MAb had no significant effect on invasion. Representative photomicrographs are also shown.

Figure 24:
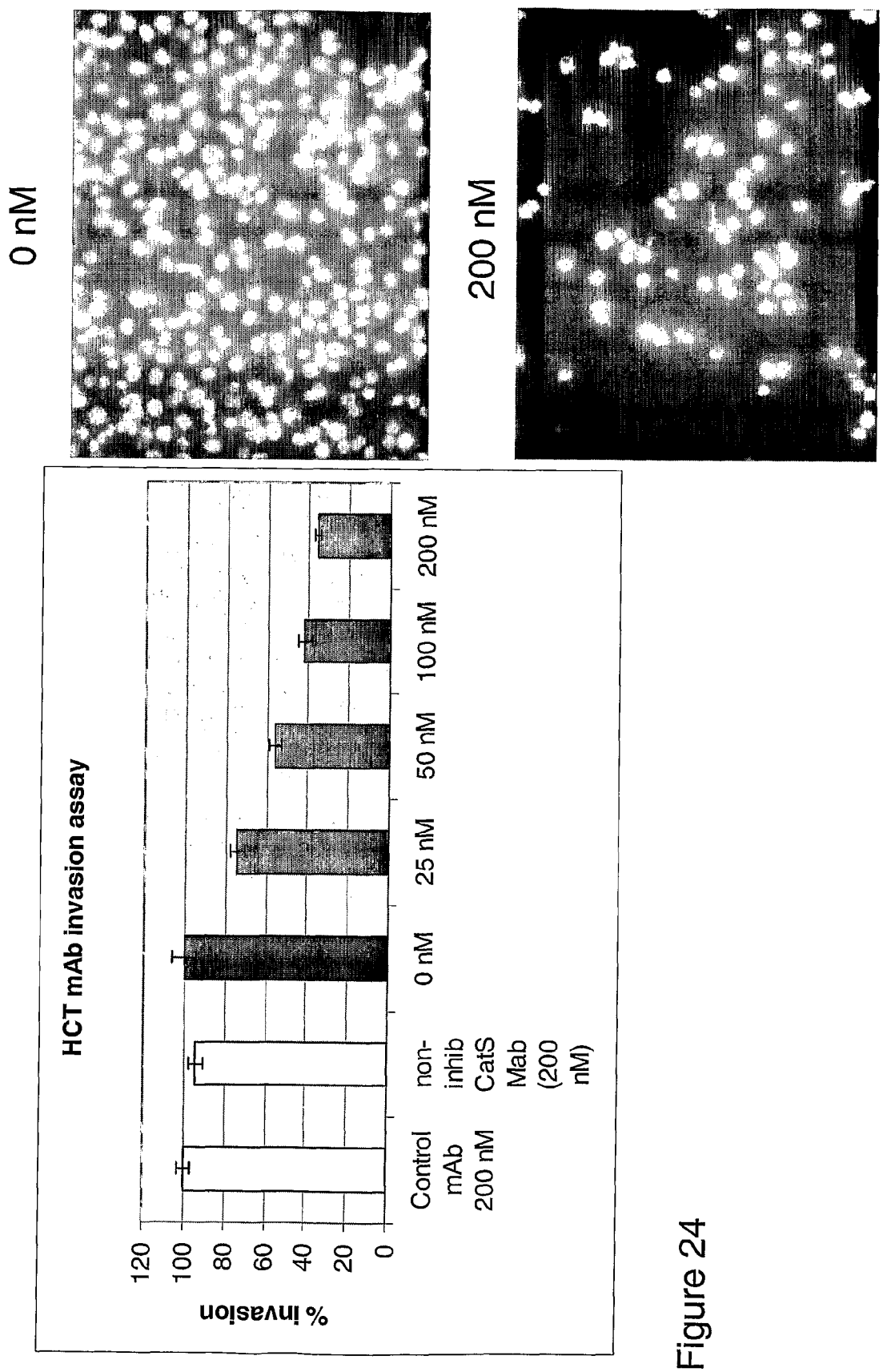

FIG. 24 illustrates the effect of the Cat S inhibitory monoclonal antibody in an in vitro invasion assay on the HCT116 colorectal carcinoma cell line. The invasion assay was performed in the presence of increasing concentrations of the inhibitory antibody (0-200 nM), showing a reduction in tumour cell invasion of up to 64%. A non-related isotype control mAb and the non-inhibitory Cat S MAb had no significant effect on invasion. Representative photomicrographs are also shown.

Figure 25:
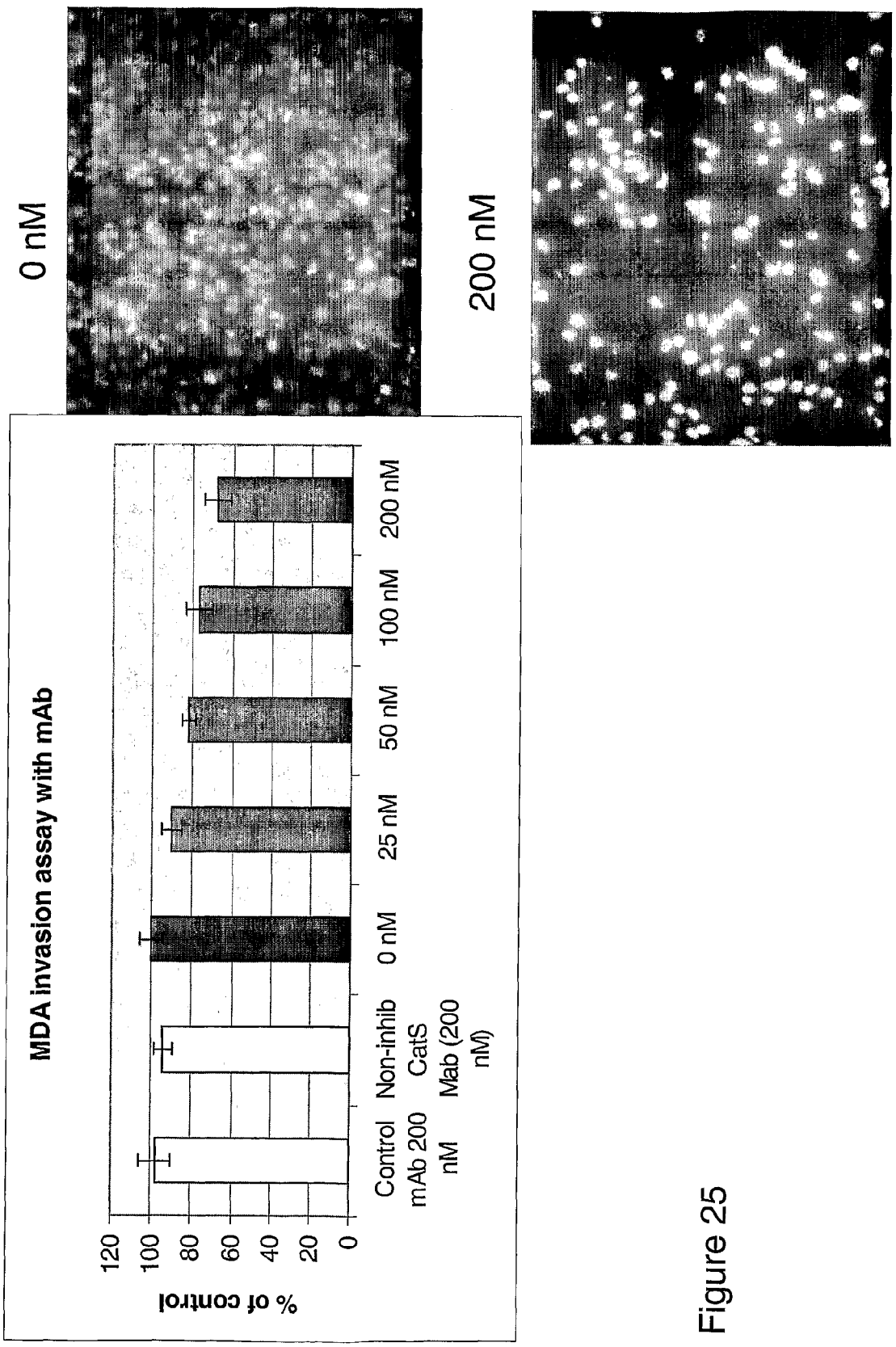

FIG. 25 illustrates the effect of the Cat S inhibitory monoclonal antibody in an in vitro invasion assay on the MDA-MB-231 breast carcinoma cell line. The invasion assay was performed in the presence of increasing concentrations of the inhibitory antibody (0-200 nM), showing a reduction in tumour cell invasion of up to 32%. A non-related isotype control mAb and the non-inhibitory Cat S MAb had no significant effect on invasion. Representative photomicrographs are also shown.

Figure 26:
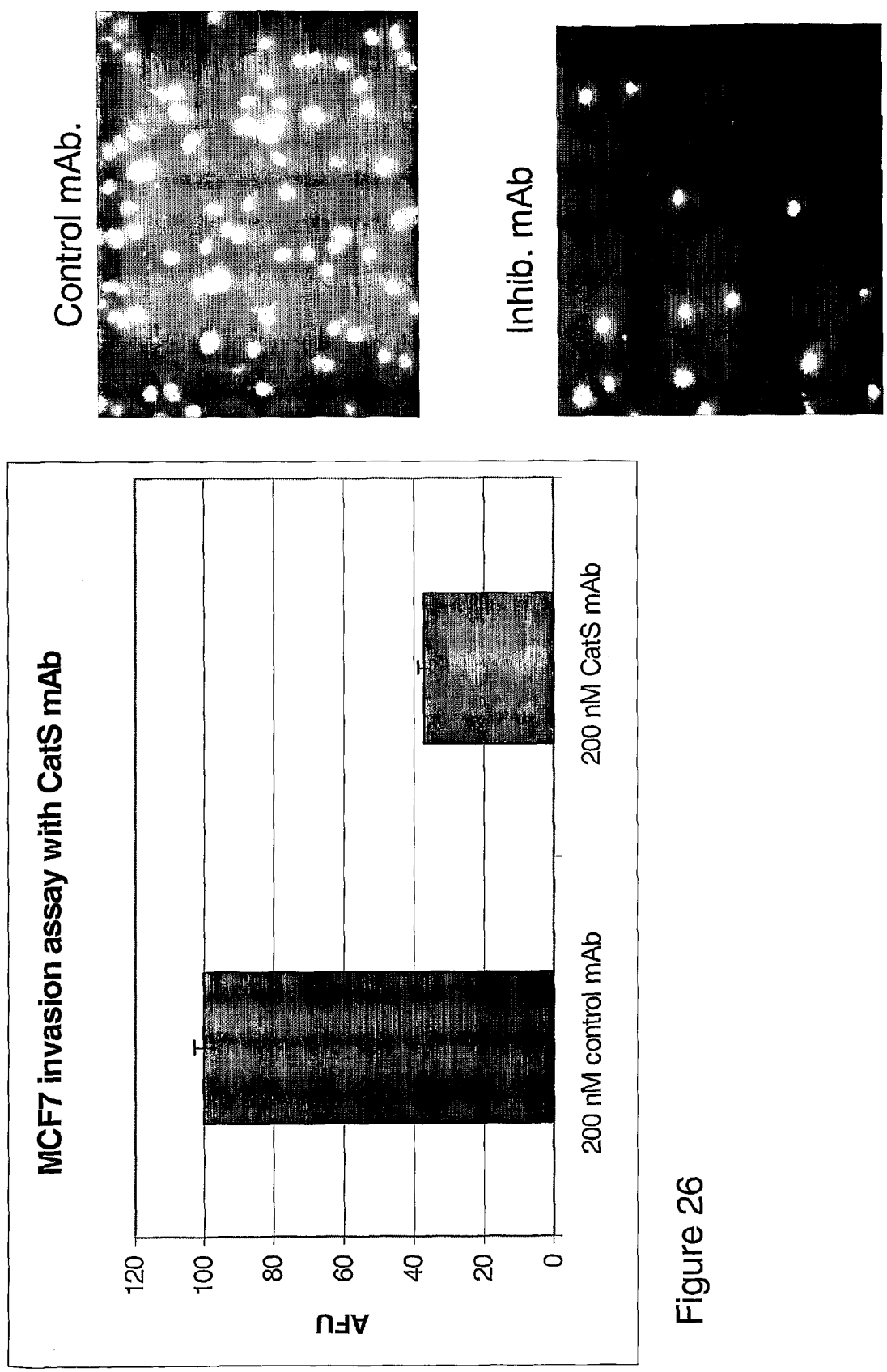

FIG. 26 illustrates the effect of the Cat S inhibitory monoclonal antibody in an in vitro invasion assay on the MCF7 breast carcinoma cell line. The invasion assay was performed in the presence of 200 nM of a control isotype monoclonal antibody and 200 nM of the inhibitory antibody, showing a reduction in tumour cell invasion of 63%. Representative photomicrographs are also shown.

FIG. 27 illustrates the results of a Matrigel assay, illustrating that capillary tubule formation is inhibited in the presence Mab 1E11.

MATERIALS AND METHODS

Cloning

Figure 1:
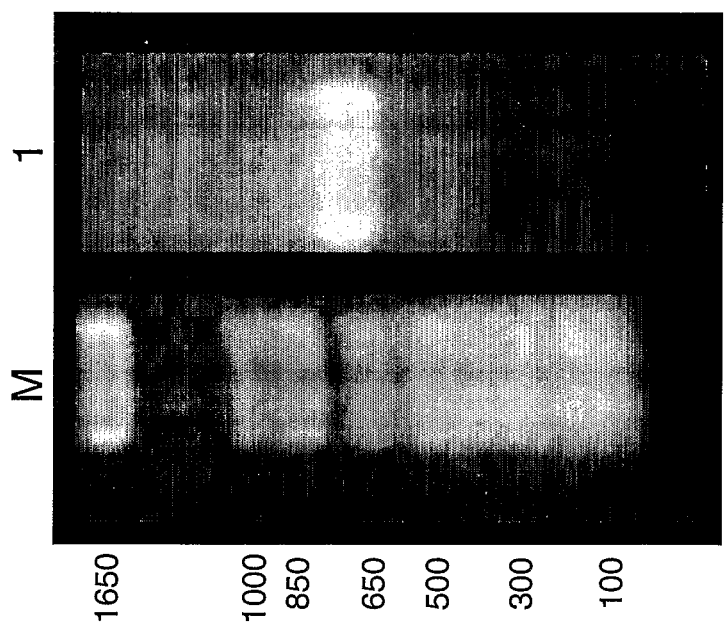
FIG. 1 illustrates PCR amplification of Cat S from a spleen cDNA library. M: DNA 1 KB plus ladder (Invitrogen); 1: PCR product corresponding to the mature Cat S gene specific sequence.

The DNA sequence encoding the mature Cat S protein was amplified by PCR from a spleen cDNA library using gene-specific primers encoding BamH1 and Sal1 restriction sites (denoted by lower case letters) (FIG. 1).

```
Sense:      TTT TTT gga tcc TTG CCT GAT TCT GTG GAC
            TGG AGA

Antisense:  TTT TTT gtc gac CTA GAT TTC TGG GTA AGA
            GG
```

The Cat S gene was cloned into the bacterial expression vector pQE30 allowing the incorporation of a hexahistidine tag onto the N-terminus of the recombinant protein. This construct was then used to transform competent TOP10F' *E. coli* cells (Invitrogen). Positive transformants were selected by colony PCR using vector-specific primers flanking the multiple cloning site (FIG. 2).

Expression of Recombinant Cat S Protein

The positive clones were propagated overnight at 37° C. in 5 mls of Luria-Bertani (LB) broth supplemented with 50 µM ampicillin. A 300 µl aliquot of this culture was retained for inoculation of secondary cultures and the remainder of the sample was miniprepped using the Qiagen miniprep kit and the sequence verified by DNA sequencing.

Three secondary cultures were inoculated to allow visualisation of protein expression. The cultures were induced with IPTG (final concentration 1 mM) when the cultures had an OD of 0.2, 0.5 and 1.0 ($A_{550}$) respectively and then left for 4 hrs at 37° C. The cells were then harvested by centrifugation at 4000 rpm for 15 mins and the pellet resuspended in 1 ml of PBS/0.1% Igepal supplemented with 1 µl of lysonase. Samples were then analysed by SDS-PAGE and western blotting to confirm expression of the protein. The SDS-PAGE gel was stained overnight in coomassie blue and destained the following day (FIG. 3).

The recombinant Cat S protein was then expressed in 500 mls of LB broth supplemented with ampicillin, using the secondary culture as an inoculant and induced with IPTG once the culture had reached the optimal optical density. The culture was centrifuged at 5000 rpm for 15 mins and the pellet retained for protein purification.

Protein Purification

The induced recombinant protein was solubilised in 50 mls of 8 M urea buffer (480 g Urea, 29 g NaCl, 3.12 g NaH2PO4 (dihydrate), 0.34 g Imidazole) overnight. The solution was centrifuged at 6000 rpm for 1 hr, after which the supernatant was filtered using 0.8 µm gyrodisc filters before purification.

The protein was purified by its N-terminal hexahistidine tag and refolded using on-column refolding by immobilized metal affinity chromatography. Chelating hi-trap columns (Amersham Biosciences) were charged using 100 mM nickel sulphate before attachment to the Aktaprime. Refolding takes place by the exchange of the 8 M urea buffer with a 5 mM imidazole wash buffer (29 g NaCl, 3.12 g NaH2PO4 (dihydrate) 0.34 g Imidazole, pH 8.0) and elution of the protein using a 500 mM imidazole elution buffer (29 g NaCl, 3.12 g NaH2PO4 (dihydrate), 34 g Imidazole). The elution profile of the purified recombinant protein was recorded and can be seen in FIG. 4a.

The eluted fractions were subjected to SDS-PAGE analysis to confirm recombinant protein presence in eluted fractions. The gels were stained with coomassie blue overnight and subsequently destained to determine the fractions containing the Cat S protein (FIG. 4b).

Antibody Generation

The refolded protein was used as an immunogen to generate monoclonal antibodies. Five BALB/C mice were immunized at three weekly intervals with 150 µg of purified recombinant protein and the antibody titre was analysed after boosts three and five. A test bleed was taken from each animal and tested at 1:1000 dilutions in western blotting against 100 ng of antigen. Blots were developed using 3,3'-diaminobenzidine (DAB) (as described earlier) (FIG. 5).

After the fifth boost, the spleen was removed from the mouse and the antibody producing B cells were fused with SP2 myeloma cells following standard protocols. Five days after the hybridoma fusion, the HAT media was refreshed and after a further five days, the plates were examined for cell growth. Clones were screened by ELISA against recombinant protein and selected positive hybridomas were cloned twice by limiting dilution.

ELISA

The monoclonal antibodies were screened by ELISA to determine which clones should be expanded. Maxi Sorb 96 well plates were coated with recombinant antigen by adding 100 µl of coating buffer (Buffer A: 0.42 g sodium bicarbonate/100 µl $H_2O$, Buffer B: 0.53 g sodium carbonate/100 µl $H_2O$, pH 9.5) containing the screening antigen to each well (100 ng/well). A control antigen was also used to eliminate non-specific clones. The plates were incubated at 37° C. for 1 hr to allow the antigen to bind to the well and then blocked for 1 hr at room temperature by adding 200 µl PBS/3% BSA to each well.

The blocking solution was removed from the plates and 100 µl of hybridoma supernatant was added to a positive antigen and a control antigen well. The screening plates were incubated with supernatant for 1 hr on a rocker at room temperature. The plates were washed three times with PBS-T, after which 100 µl of goat anti-mouse HRP conjugated secondary antibody (1:3000) was added to each well and incubated for 1 hr at room temperature. The plates were washed three times with PBS-T and 100 µl of 3,3',5,5'-tetramethylbenzidine (TMB) was added to each well and incubated for 5 mins at 37° C. Positive wells were indicated by a colour development and the reaction was stopped by addition of 50 µl 1M HCL. Plates were read by a spectrophotometer at 450 nm and samples displaying a positive reading in the screening well (+) with a negative reading in the control well (−) were chosen for further work (FIG. 6). The cells from the original wells were transferred into a 24 well plate and grown up.

Western Blotting

The supernatants from the hybridoma cell lines were analysed by western blotting to determine the ability of the monoclonal antibodies to detect endogenous native Cat S protein in the U251 mg grade IV astrocytoma cell line, in which Cat S is highly expressed. A 30 µg/ml aliquot of U251 mg whole cell lysate was separated by SDS-PAGE and transferred onto Hybond-C Extra nitrocellulose membrane (Amersham Biosciences). The membrane was blocked by incubation in PBS/5% marvel for 1 hr at room temperature, after which it was rinsed briefly in PBS. The monoclonal antibodies were used at a 1:500 dilution in PBS and incubated on the membrane overnight at 40° C. while gently rocking. The blot was then rinsed three times with PBS/1% marvel and 0.1% Tween-20 and then incubated with the goat anti-mouse HRP conjugated secondary antibody at a 1:3000 dilution for 1 hr at room temperature while shaking. The blot was then rinsed three times with the PBS/1% marvel and 0.1% Tween-20 solution, followed by a short rinse in PBS. The blot was incubated with ECL plus substrate (Amersham Biosciences) for 5 mins at room temperature before development using Kodak photographic film under safe light conditions (FIG. 7).

High Throughput Screening to Identify Potential Inhibitory Antibodies

The inhibitory effect of the monoclonal antibodies were determined by a fluorometric assay, using a Cat S synthetic substrate Z-Val-Val-Arg-AMC (Bachem) and recombinant human Cat S (Calbiochem). The recombinant Cat S enzyme was activated at 37° C. in sodium acetate buffer (100 mM sodium acetate, 1 mM EDTA, 0.1% Brij90, pH 5.5), and 2 mM dithiothreitol (DTT) for 30 mins prior to assay. Assays were carried out using 190 µl of sodium acetate/DTT buffer (90:1), 1 µl of activated Cat S, 12.5 µl of 10 mM Cbz-Val-Val-Arg-AMC substrate and 50 µl of non-purified monoclonal antibody supernatant. Fluorescence was measured at 375 nm excitation and 460 nm emission wavelengths every 5 mins for 4 hrs (FIG. 8). From this five monoclonal antibody secreting cell lines were selected for large-scale growth, purification. The hybridoma supernatant was purified by affinity chromatography using either an protein G or protein M column (dependent on isotyping results) (representative FIG. 9).

Isotyping of Monoclonal Antibodies

The monoclonal antibodies selected for large scale growth were isotyped prior to purification using the ImmunoPure® monoclonal antibody isotyping kit from Pierce. Ten wells on a 96-well plate were coated with 50 µl of a goat anti-mouse coating antibody and incubated at room temperature for 2 hrs. The wells were blocked to prevent non-specific binding, using 125 µl of blocking solution and incubated at room temperature for 1 hr. The wells were then washed four times with 125 µl of wash buffer. Nine of the ten wells were incubated with 50 µl of hybridoma supernatant, with 50 µl of positive control solution added to the tenth well and incubated at room temperature for 1 hr. The wells were washed once again using 125 µl of wash buffer before addition of 50 µl of subclass-specific anti-mouse immunoglobulins and controls to the ten separate wells and incubated at room temperature for 1 hr. The wells were washed four times with 125 µl of wash buffer, after which 100 µl of ABTS substrate solution was added to each well and allowed to react at room temperature for 30 mins. The results were read using a spectrophotometer at 405 nm (FIG. 10).

Fluorometric Assay

The purified monoclonal antibodies were analysed by fluorometric assay for quantification of their ability to inhibit the activity of Cat S. The principles of this assay are the same as that previously used. Fluorescence was measured at 375 nm excitation and 460 nm emission wavelengths every minute for 1 hr. (FIG. 11). These progress curves are indicative of the action of a slow-binding reversible inhibitor. The apparent first order rate order curves produced were then subjected to non-linear regression analysis (Morrison and Walsh, 1988) using GraFit software as shown (FIG. 12), producing a $K_i$ of 533 nM. Control fluorometric assays using cathepsins L and K were performed as described above using 50 μM of the fluorogenic substrate Cbz-Phe-Arg-AMC (FIGS. 14 and 15), demonstrating that the inhibitory activity towards Cat S was indeed specific.

Specificity of Antibody Binding

Western blots were performed as described before to show specificity of the antibody binding to Cat S and not to CatB, L or K. Briefly, 100 ng of recombinant CatS Cat S, K, L and B were loaded onto a SDS-PAGE gel, then transferred onto Hybond-C Extra nitrocellulose membrane (Amersham Biosciences). The membrane was blocked by incubation in PBS/5% marvel for 1 hr at room temperature, after which it was rinsed briefly in PBS. The monoclonal antibodies were used at a 1:500 dilution in PBS and incubated on the membrane overnight at 4° C. while gently rocking. The blot was then rinsed three times with PBS/1% marvel and 0.1% Tween-20 and then incubated with the goat anti-mouse HRP conjugated secondary antibody at a 1:3000 dilution for 1 hr at room temperature while shaking. The blot was then rinsed three times with the PBS/1% marvel and 0.1% Tween-20 solution, followed by a short rinse in PBS. The blot was incubated with ECL plus substrate (Amersham Biosciences) for 5 mins at room temperature before development using Kodak photographic film under safe light conditions (FIG. 15).

Specificity of binding was also determined by Antigen-immobilised ELISAs. These were performed as described earlier to determine specificity and affinity of the antibody for Cat S. To determine specificity, 96-well plates were coated with 100 ng/well of cathepsins S, L, K and B in duplicate and incubated with predetermined concentrations of the Cat S mAb ($1\times10^{-7}$ to $1\times10^{31\ 12}$) (FIG. 16).

In addition the ability of the antibody to bind to CatS S was also examined in a pH range. This ELISA was performed on a 96-well plates coated with 100 ng/well of Cat S antigen and incubated with predetermined concentrations of the Cat S mAb ($1\times10^{-7}$ to $1\times10^{-12}$) in a services of different pH points applying the antibody dilutions to the plate in 50 mM Bis-Tris.HCl buffer adjusted to the given pH points, allowing antibody affinity to be determined (FIG. 17). From this it was clear that binding was similar at pH 5.5 to 7.5, but slightly reduced at pH 4.9.

Monoclonal Sequencing

For the sequencing of the inhibitory monoclonal antibody, the RNA was extracted from the hybridoma cell line and the VH and VL regions amplified by RT-PCR (FIG. 18). The PCR products were cloned using the TOPO TA kit from Invitrogen and positive colonies were verified by colony PCR using vector specific primers (FIG. 19) and DNA sequencing to derived the consensus sequence of the VH (Seq ID No: 7) and VL (Seq ID No: 8) regions of the inhibitory monoclonal antibody (FIG. 20).

Confirmation of the Presence of Cat S in Tumour Cell Lines by RT-PCR

RNA was extracted from U251 mg, MCF7, HCT116 and PC3 cell lines using the Absolutely RNA™ RT-PCR Miniprep kit (Stratagene) according to manufacturer's instructions and quantified using a spectrophotometer. RT-PCR was performed using the One-Step RT-PCR kit (Qiagen) under the following conditions: 50° C. for 30 min, 95° C. for 15 min, and 40 cycles of 94° C. for 1 min, 55° C. for 1 min 30 sec and 72° C. for 1 min, followed finally by a 72° C. for 10 min. Primer sequences for Cat S were as follows; Cat S F: GGG-TACCTCATGTGACAAG (Seq ID No: 11), Cat S R: TCACTTCTTCACTGGTCATG (Seq ID No: 12); Amplification of the β-actin gene was used as an internal control to demonstrate equal loading; Actin F: ATCTGGCACCACAC-CTTCTACAATGAGCTGCG (Seq ID No: 13) Actin R: CGTCATACTCCTGCTTGCTGATCCACATCTGC (Seq ID No: 14). RT-PCR products were analysed by agarose gel electrophoresis (FIG. 21).

In-Vitro Invasion Assays

In-vitro invasion assays were performed using a modified Boyden chamber with 12-μm pore membranes (Costar Transwell plates, Corning Costar Corp., Cambridge, Mass., USA). The membranes were coated with Matrigel (100 μg/cm$^2$) (Becton Dickinson, Oxford, UK) and allowed to dry overnight in a laminar flow hood. Cells were added to each well in 500 μl of serum-free medium in the presence of predetermined concentrations of the Cat S inhibitory antibody or control antibody. All assays were carried out in triplicate and invasion plates were incubated at 37° C. and 5% $CO_2$ for 24 hours after which cells remaining on the upper surface of the membrane were removed and invaded cells fixed in Carnoy's fixative for 15 minutes. After drying, the nuclei of the invaded cells were stained with Hoechst 33258 (50 ng/ml) in PBS for 30 minutes at room temperature. The chamber insert was washed twice in PBS, mounted in Citifluor and invaded cells were viewed with a Nikon Eclipse TE300 fluorescent microscope. Ten digital images of representative fields from each of the triplicate membranes were taken using a Nikon DXM1200 digital camera at magnification of ×20. The results were analysed using Lucia GF 4.60 by Laboratory Imaging and were expressed as a percentage of invaded cells (FIGS. 22-26).

Capillary-Like Tube Formation Assay

The anti-angiogenic properties of the Cat S mAb was assessed using a HUVEC cells microtubule formation assay. The effect of the antibody on endothelial cell tube formation was assessed as follows: Two hundred microliter of Matrigel (10 mg/ml) was applied to pre-cooled 48-well plates, incubated for 10 min at 4° C. and then allowed to polymerize for 1 h at 37° C. Cells were suspended in endothelial growth cell medium MV (Promocell), containing 200 nM of the appropriate antibody. Five hundred microliter ($1\times10^5$ cells) was added to each well. As controls, cells were incubated with vehicle-only control medium containing the appropriate volumes of PBS. After 24 h incubation at 37° C. and 5% CO2, cells were viewed using a Nikon Eclipse TE300 microscope.

Cells grown in the presence of the 1E11 Mab displayed an inability to form microtubules indicating that Cat S specific antibodies have the ability to disrupt microtubule formation, indicating anti-tumourogenic properties influencing cell migration and angiogenisis (FIG. 27). Cells grown in the presence of an isotype control antibody displayed normal microtubule formation.

All documents referred to in this specification are herein incorporated by reference. Various modifications and variations to the described embodiments of our disclosures will be apparent to those skilled in the art without departing from the scope and spirit of our disclosure. Although our disclosure has been described in connection with specific preferred embodiments, it should be understood that disclosure as claimed should not be unduly limited to such specific embodiments. Indeed, various modifications of the described modes of carrying out our disclosure which are obvious to those skilled in the art are intended to be covered by our disclosure.

REFERENCES

Baker C A, Martin D and Manuelidis L. Microglia from Creutzfeldt-Jakob Disease-infected brains are infectious and show specific mRNA activation profiles. *J. Virology.* 2002, 76, 10905-10913.

Baker S M, Karlsson L and Thurmond R L. Cloning, expression, purification, and activity of dog (*Canis familiaris*) and monkey (*Saimiri boliviensis*) cathepsin S. *Prot Exp Pur.* 2003; 28: 93-101.

Beck H, Schwarz G, Schröter C J, et al. Cathepsin S and an asparagines-specific endoprotease dominate the proteolytic processing of human myelin basic protein in vitro. *Eur. J. Immunol.* 2001; 31: 3726-3736.

Berdowska, I. Cysteine proteases as disease marker. *Clinica Chimica Acta.* 2004; 342: 41-69.

Chapman H A, Riese J R and Shi G P. Emerging roles for cysteine proteinases in human biology. *Ann Rev Physiol.* 1997; 59: 63-88.

Fan X, Kopitar-Jerala N, Premzl A, Bestagno M, Burrone O and Kos J. Molecular cloning and chimerisation of an inhibitory anti-cathepsin B antibody and its expression in Chinese hamster ovary cells. *Biol. Chem.* 2002; 383: 1817-1820.

Fernandez P L, Farre X, Nadal A, et al. Expression of cathepsins B and S in the progression of prostate carcinoma. *Int J Cancer.* 2001; 95: 51-55.

Flannery T, Gibson D, Mirakhur M, et al. The clinical significance of cathepsin S expression in human astrocytomas. *Am J Pathol.* 2003; 163: 175-182.

Hashimoto Y, Kakegawa H, Narita Y et al. Significance of cathepsin B accumulation in synovial fluid of rheumatoid arthritis. *Biochem. Biophys. Res. Commun.* 2001; 283: 334-339.

Katunuma N, Matsunaga Y, Himeno K and Hayashi Y. Insights into the roles of cathepsins in antigen processing and presentation revealed by specific inhibitors. *Biol. Chem.* 2003; 384: 883-890.

Kos J, Sekirnik A, Kopitar G, et al. Cathepsin S in tumours, regional lymph nodes and sera of patients with lung cancer: relation to prognosis. Br. J. Cancer. 2001, Kos J, Sekirnik A, Kopitar G, et al. Cathepsin S in tumours, regional lymph nodes and sera of patients with lung cancer: relation to prognosis. *Br J Cancer.* 2001; 85: 1193-1200.

Lemere C A, Munger J S, Shi G P, et al. The lysosomal cysteine protease, cathepsin S, is increased in Alzheimer's disease and Down syndrome brain. An immunocytochemical study. *Am. J. Pathol.* 1995; 146: 848-60.

Liuzzo J P, Pentanceska S S, Moscatelli D and Devi L A. Inflammatory mediators regulate cathepsin S in macrophages and microglia: a role in attenuating heparan sulfate interactions. *Molecular Med.* 1999; 5: 320-333.

Mikkelsen T, Yan P S, Ho K L, Sameni M, Sloane B F and Rosenblum M L. Immunolocalization of cathepsin B in human glioma: implications for tumor invasion and angiogenesis. *J Neurosurg.* 1995; 83: 285-290.

Morrison J F, Walsh C T. (1988). The behaviour and significance of slow-binding enzyme inhibitors. *Adv Enzymol Relat Areas Mol. Biol.* 61, 201-301.

Munger J S, Haass C, Lemere C A, et al. Lysosomal processing of amyloid precursor protein to Aβ peptides: a distinct role of cathepsin S. *Biochem. J.* 1995; 311: 299-305.

Nakagawa T Y, Brissette W H, Lira P D, et al. Impaired invariant chain degradation and antigen presentation and diminished collagen-induced arthritis in cathepsin S null mice. *Immunity.* 1999; 10: 207-217.

Palmer J T, Rasnick D, Klaus J L and Bromme D. Vinyl sulfones as mechanism-based cysteine protease inhibitors. *J. Med. Chem.* 1995; 38: 3193-3196.

Premzl A, Zavašnik-Bergant V, Turk V and Kos J. Intracellular and extracellular cathepsin B facilitate invasion of MCF-10A neoT cells through reconstituted extracellular matrix in vitro. *Exp. Cell Res.* 2003; 283: 206-214.

Rawlings N D and Barrett A J. MEROPS: the peptidase database. *Nucleic Acids Res.* 1999; 27: 325-331.

Seliger B, Maeurer M J and Ferrone S. Antigen-processing machinery breakdown and tumour growth. *Immunology Today.* 2000; 21: 455-464.

Shi G P, Munger J S, Meara J P, Rich D H and Chapman H A. Molecular cloning and expression of human alveolar macrophage cathepsin S, an elastinolytic cysteine protease. *J Biol. Chem.* 1992; 267: 7258-7262.

Sivaparvathi M, Yamamoto M, Nicolson G L, et al. Expression and immunohistochemical localization of cathepsin L during the progression of human gliomas. *Clin Exp Metastasis.* 1996; 14: 27-34.

Sukhova G K, Shi G P, Simon D I, Chapman H A and Libby P. Expression of the elastolytic cathepsins S and K in human atheroma and regulation of their production in smooth muscle cells. *J. Clin. Invest.* 1998; 102: 576-83.

Sukhova G K, Zhang Y, Pan J H, et al. Deficiency of cathepsin S reduces atherosclerosis in LDL receptor-deficient mice. *J. Clin. Invest.* 2003; 111: 897-906.

Sun J, Pons J and Craik C S. Potent and selective inhibition of membrane-type serine protease 1 by human single-chain antibodies. *Biochemistry.* 2003; 42: 892-900.

Takeuchi T, Harris J L, Huang W, Yan K W, Coughlin S R and Craik C S. Cellular localization of membrane-type serine protease 1 and identification of protease-activated receptor-2 and single-chain urokinase-type plasminogen activator as substrates. J. Biol. Chem. 2000; 275: 26333-26342.

Thurmond R L, Sun S, Sehon C A et al. Identification of a potent and selective noncovalent cathepsin S inhibitor. *J. Pharm. Exp. Therap.* 2003; 308: 268-276.

Walker B, Lynas J F, Meighan M A and Bromme D. Evaluation of dipeptide α-keto-β-aldehydes as new inhibitors of Cathepsin S. *Biochem. Biophys. Res. Comm.* 2000; 75: 401-405.

Wiendl H, Lautwein A, Mitsdörffer M, et al. Antigen processing and presentation in human muscle: cathepsin S is critical for MHC class II expression and upregulated in inflammatory myopathies. *J. Neuroimmun.* 2003; 138: 132-143.

The invention claimed is:

1. An isolated specific binding member which binds cathepsin S and inhibits its proteolytic activity, wherein the specific binding member comprises an antigen binding domain comprising (i) a CDR with the amino acid sequence shown in Seq ID No: 1, a CDR with the amino acid sequence shown in Seq ID No: 2, and a CDR with the amino acid sequence shown in Seq ID No: 3 as CDRs 1, 2 and 3 respectively; and (ii) a CDR with the amino acid sequence shown in Seq ID No: 4, a CDR, with the amino acid sequence shown in Seq ID No: 5, and a CDR with the amino acid sequence shown in Seq ID No: 6 as CDRs 1, 2 and 3 respectively.

2. The specific binding member according to claim 1, wherein the antibody $V_H$ domain comprises CDRs with the amino acid sequences shown in Seq ID No: 1, Seq ID No: 2 and Seq ID No: 3 as CDRs 1, 2 and 3 respectively.

3. The specific binding member according to claim 2 wherein the antibody $V_H$ domain comprises the amino acid sequence shown in Seq ID No: 7.

4. The specific binding member according to claim 1, wherein the antibody $V_L$ domain comprises CDRs with the amino acid sequences shown in Seq ID No: 4, Seq ID No: 5 and Seq ID No: 6 as CDRs 1, 2 and 3 respectively.

5. The specific binding member according to claim 1 wherein the antibody $V_L$ domain comprises the amino acid sequence shown in Seq ID No: 8.

6. The specific binding member according to claim 1, wherein the specific binding member inhibits the proteolytic activity of cathepsin S with a potency at least 25% of that of an antibody comprising an antibody $V_H$ domain having the amino acid sequence shown in Seq ID No: 7 and an antibody $V_L$ domain having the amino acid sequence shown in Seq ID No: 8.

7. The specific binding member according to claim 1, wherein the specific binding member is a whole antibody.

8. The specific binding member according to claim 1, wherein the specific binding member comprises an scFv antibody molecule.

9. A pharmaceutical composition comprising a specific binding member according to claim 1.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      CDR amino acid sequence

```
<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR amino acid sequence

<400> SEQUENCE: 2

Tyr Ile Thr Thr Gly Gly Val Asn Thr Tyr Tyr Pro Asp Thr Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      CDR amino acid sequence

<400> SEQUENCE: 3

His Ser Tyr Phe Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR amino acid sequence

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR amino acid sequence

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR amino acid sequence

<400> SEQUENCE: 6

Ser Gln Thr Thr His Val Pro Pro Thr
1               5

<210> SEQ ID NO 7
<211> LENGTH: 114
```

```
<212> TYPE: PRT
<213> ORGANISM: Artificial Sequence
<220> FEATURE:
<223> OTHER INFORMATION: Description of Artificial Sequence: Synthetic
      VH domain amino acid sequence

<400> SEQUENCE: 7

Val Gln Leu Gln Glu Ser Gly Gly Val Leu Val Lys Pro Gly Gly Ser
1               5                   10                  15

Leu Lys Leu Ser Cys Ala Ala Ser Gly Phe Ala Phe Ser Tyr Asp
            20                  25                  30

Met Ser Trp Val Arg Gln Thr Pro Glu Lys Arg Leu Glu Trp Val Ala
        35                  40                  45

Tyr Ile Thr Thr Gly Gly Val Asn Thr Tyr Tyr Pro Asp Thr Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Lys Ser Glu Asp Thr Ala Met Tyr Tyr Cys Ala
                85                  90                  95

Arg His Ser Tyr Phe Asp Tyr Trp Gly Gln Gly Thr Thr Val Thr Val
            100                 105                 110

Ser Ser

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      VL domain amino acid sequence

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Pro Thr Phe Gly Ser Gly Thr Lys Leu Glu Ile Lys
            100                 105                 110

Arg

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      sense CatS-specific primer incorporating BamHI restriction site

<400> SEQUENCE: 9 tttttttggat ccttgcctga ttctgtggac tggaga                              36

<210> SEQ ID NO 10
```

-continued

```
<211> LENGTH: 32
<212> TYPE: DNA
<213> ORGANISM: Artificial Sequence
<220> FEATURE:
<223> OTHER INFORMATION: Description of Artificial Sequence: Synthetic
      antisense CatS-specific primer incorporating SalI restriction
      site

<400> SEQUENCE: 10 tttttttgtcg acctagattt ctgggtaaga gg                                     32

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      CatS F oligonucleotide

<400> SEQUENCE: 11
gggtacctca tgtgacaag                                                     19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      CatS R oligonucleotide

<400> SEQUENCE: 12
tcacttcttc actggtcatg                                                    20

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      Actin F oligonucleotide

<400> SEQUENCE: 13
atctggcacc acaccttcta caatgagctg cg                                      32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      Actin R oligonucleotide

<400> SEQUENCE: 14
cgtcatactc ctgcttgctg atccacatct gc                                      32
```